(12) United States Patent
Baginski

(10) Patent No.: US 8,445,292 B2
(45) Date of Patent: May 21, 2013

(54) COMPOUNDS AND METHODS FOR RAPID LABELING OF N-GLYCANS

(75) Inventor: Tomasz Baginski, Mountain View, CA (US)

(73) Assignee: ProZyme, Inc., Hayward, CA (US)

( * ) Notice: Subject to any disclaimer, the term of this patent is extended or adjusted under 35 U.S.C. 154(b) by 46 days.

(21) Appl. No.: 13/244,454

(22) Filed: Sep. 24, 2011

(65) Prior Publication Data

US 2012/0107942 A1 May 3, 2012

Related U.S. Application Data

(62) Division of application No. 12/365,880, filed on Feb. 4, 2009, now Pat. No. 8,124,792.

(60) Provisional application No. 61/026,080, filed on Feb. 4, 2008.

(51) Int. Cl.
*C07D 207/46* (2006.01)
*G01N 21/64* (2006.01)

(52) U.S. Cl.
USPC .......................................... 436/172; 548/542

(58) Field of Classification Search
USPC .......................................... 548/542; 436/172
See application file for complete search history.

(56) References Cited

U.S. PATENT DOCUMENTS

| | | | |
|---|---|---|---|
| 4,003,912 | A | 1/1977 | Franz |
| 5,283,353 | A | 2/1994 | Rasmussen |
| 5,296,599 | A | 3/1994 | Cohen et al. |
| 2001/0026929 | A1 | 10/2001 | Yang et al. |
| 2005/0079624 | A1* | 4/2005 | Miyano et al. ............ 436/96 |
| 2005/0158708 | A1 | 7/2005 | Alroy et al. |

FOREIGN PATENT DOCUMENTS

| | | |
|---|---|---|
| EP | 0606925 B | 10/1988 |
| EP | 0 533 200 A1 | 3/1993 |
| EP | 1 475 632 A1 | 11/2004 |
| JP | 10-306075 A | 11/1998 |
| WO | 8804323 A1 | 6/1988 |
| WO | WO 2004/027388 A2 | 4/2004 |
| WO | WO 2004/027388 A3 | 4/2004 |

OTHER PUBLICATIONS

Breitling, R. et al., "Non-pathogenic trypanosomatid protozoa as a platform for protein research and production," *Protein Expression & Purification*, Jul. 2002, vol. 25, No. 2, pp. 209-218.

Cohen, S.A. et al., "Synthesis of a Fluorescent Derivatizing Reagent, 6-Aminoquinolyl-*N*-Hydroxysuccinimidyl Carbamate, and Its Application for the Analysis of Hydrolysate Amino Acids via High-Performance Liquid Chromatography," *Analytical Biochemistry*, 1993, vol. 211, pp. 279-287.

Guichard, G. et al., "Effective Preparation of *O*-Succinimidyl-2-(*tert*-butoxycarbonylamino)ethylcarbamate Derivatives from β-Amino Acids. Application to the Synthesis of Urea-Containing Pseudopeptides and Oligoureas," *J. Org. Chem.*, 1999, vol. 64, pp. 8702-8705.

International Search Report mailed on May 8, 2009, for International Application No. PCT/US2009/033112 filed on Feb. 4, 2009, 4 pages.

Iwaki, K. et al., "Amino Acid Analysis by Reversed-Phase High-Performance Liquid Chromatography, Automatic Pre-Column Derivatization With Activated Carbamate Reagent," *Journal of Chromatography*, 1987, vol. 407, pp. 273-279.

Nimura, N. et al., "Activated Carbamate Reagent as Derivatizing Agent for Amino Compounds in High-Performance Liquid Chromatography," *Analytical Chemistry*, Oct. 1986, vol. 58, No. 12, pp. 2372-2375.

Takeda, K. et al., "Convenient Methods for Sytheses of Active Carbamates, Ureas and Nitrosoureas Using N,N'-disuccinimido Carbonate (DSC)," *Tetrahedron Letters*, 1983, vol. 24, No. 42, pp. 4569-4572.

Vasilevich; N.I. et al., "Conversion of *O*-succinimidyl carbamates to *N*-(*O*-carbamoyl)-succinmonoamides and ureas: effects of *N*-substituents and reaction conditions on the reaction pathway," *Tetrahedron Letters*, 2002, vol. 43, pp. 6649-6652.

Weitzhandler, M. et al., "Monosaccharide and Oligosaccharide Analysis of Proteins Transferred to Polyvinylidene Fluoride Membranes after Sodium Dodecyl Sulfate-Polyacrylamide Gel Electrophoresis," *The Journal of Biological Chemistry*, Mar. 5, 1993, vol. 268, No. 7, pp. 5121-5130.

Rasmussen et al., "Identification and Derivitization of (Oligosaccharyl)amines Obtained by Treatment of Asparagine-Linked Glycopeptides with N-GLYCANASE Enzyme," J Amer Chem Soc, 1992, pp. 1124-1126, v. 114.

Heinze-Krauss et al. (J. Med. Chem., 1998, v. 41, n. 21, p. 3961-3971).

* cited by examiner

*Primary Examiner* — Robert Havlin
(74) *Attorney, Agent, or Firm* — Laurence J. Hyman; Hyman IP Law

(57) ABSTRACT

The present invention provides compounds and methods for rapid labeling of N-glycans, for example, rapid fluorescent labeling of N-glycans. In one aspect, the present invention provides fluorescent carbamate or thiocarbamate compounds. Upon contacting with N-glycans, the compounds undergo facile reactions with N-glycans to form fluorescent-labeled N-glycans.

31 Claims, 8 Drawing Sheets

COMPOUNDS AND METHODS FOR RAPID LABELING OF N-GLYCANS

CROSS-REFERENCES TO RELATED APPLICATIONS

This application is a divisional of U.S. Patent Application Ser No. 12/365,880, filed Feb 4, 2009, which claims priority to U.S. Provisional Patent Application No. 61/026,080, filed Feb 4, 2008. The contents of each of these applications are hereby incorporated in their entirety for all purposes.

BACKGROUND OF THE INVENTION

There is a considerable interest by biochemists, clinical chemists and pharmaceutical manufacturers in determining the distribution profiles of N-glycans in biological samples, such as for example therapeutic glycoproteins. Glycosylation profile of therapeutic proteins needs to be monitored during development to ensure proper biological properties and during a production, to ensure consistency of the therapeutic product. N-glycans released from glycoproteins by enzymatic cleavage with PNGase F (Peptide-N4-(acetyl-β-glucosaminyl)-asparagine amidase, EC 3.5.1.52) are typically labeled at their free-reducing terminus with fluorescent dyes for analysis by methods such as high performance liquid chromatography (HPLC), capillary electrophoresis (CE), carbohydrate gel electrophoresis, mass spectrometry and others. Fluorescent labeling of glycans facilitates their sensitive detection as well as contributes to improved resolution. PNGase F-released N-glycans are most commonly labeled by reductive amination, where the free-reducing end of a glycan is conjugated to the free amino group of a fluorescent dye. Fluorescent labeling of glycans by reductive amination usually requires anhydrous conditions, elevated temperatures and extended incubation times, which may result in a partial degradation of biologically important, labile constituents of N-glycans, for example, sialic acids.

PNGase F releases N-glycans from glycoproteins initially as β-glycosylamines, where the free-reducing end of the released glycan is conjugated with ammonia (see, Tarentino, et al. *TIGG* 1993, 23, 163-170; Rasmussen J. R. *J. Am. Chem. Soc.* 1992, 114, 1124-1126; Risley, et al. *J. Biol. Chem.* 1985, 260, 15488-15494, 1985). The stability of glycosylamines is dependent on the pH and lower pH favors rapid hydrolysis of glycosylamines to glycans with free-reducing ends and ammonia. At elevated pH, glycosylamines are stable and hydrolyze slowly, which allows glycans released as glycosylamines to be labeled with reagents reactive toward the amino groups instead of the free-reducing ends. Derivatization of glycosylamines with a number of amine-reactive reagents has been reported (for derivatization with phenylisothiocyanate, see, Rasmussen, J. R. *J. Am. Chem. Soc.* 1992, 114, 1124-1126; for derivatization with FMOC-Cl, see, Kamoda, et al. *J Proteome Res.* 2005, 4(1):146-52; for derivatization with FMOC-Cl and other dyes see Kurihara T. et al. Anal. Chem. 2007, 79(22):8694-8).

Non-fluorescent and fluorescent activated carbamate reagents are useful for derivatization of amino groups and for spectrophotometric and fluorometric detection of amino acids (see, Nimura, et al. *Anal. Chem.* 1986, 58, 2372-2375; Iwaki, et al. *J. Chromatography* 1987, 407, 273-279, 1987; Cohen, et al. Analytical Biochemistry 1993, 211, 279-287; and U.S. Pat. No. 5,296,599).

Therefore, there is a need in the art for dyes and methods that are capable of rapid labeling of glycans under mild conditions, without causing the degradation of biologically active labile components, and can provide high sensitivity of detection and high resolution during separation of glycans. Surprisingly, the present invention meets these and other needs.

BRIEF SUMMARY OF THE INVENTION

The present invention relates to compounds and methods for rapid labeling of N-glycans. In particular, the compounds are fluorescent monocyclic aromatics. Advantageously, the N-glycans sample is easy to prepare and the methods allow rapid and facile labeling of N-glycans without any degradation of the samples.

In one aspect, the present invention provides a compound of formula I:

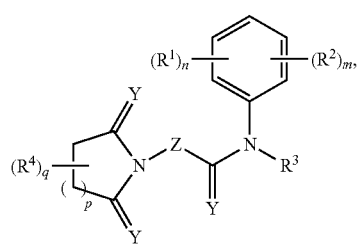

wherein:
each Y is independently O= or S=;
Z is —O— or —S—;
each $R^1$ is independently selected from the group consisting of $C_{1-8}$alkyl, $C_{1-8}$heteroalkyl and aryl; optionally, adjacent $R^1$ groups together with the benzene ring to which they are attached form a fused carbocyclic aromatic ring system having from 1-4 $R^5$ substituents selected from the group consisting of —COOH, —COO$^-$M$^+$, sulfo, alkylsulfo, phosphono and alkylphosphono. In some embodiments, the fused carbocyclic aromatic ring system is selected from the group consisting of naphthalene, phenanthrene, anthracene, triphenylene and pyrene.
each $R^2$ is independently selected from the group consisting of aryl, heteroaryl, —OR$^a$, —OC(O)OR$^a$, —OC(O)R$^a$, —OC(O)NR$^a$R$^b$, —SR$^a$, —S(O)R$^a$, —S(O)$_2$R$^a$, —S(O)$_2$NR$^a$R$^b$, —NR$^a$S(O)$_2$R$^b$, —C(O)NR$^a$R$^b$, —C(O)R$^a$, —C(O)SR$^a$, —C(=S)R$^a$, —NR$^a$C(O)R$^a$, —NR$^a$C(O)NR$^a$R$^b$, —CO$_2$R$^a$, —NR$^a$CO$_2$R$^b$, —CN, —NO$_2$, —N(R$^a$)$_2$, —NR$^a$S(O)NR$^a$R$^b$, —NR$^a$R$^b$C(=NR$^b$)NR$^a$R$^b$, —N$_3$, —NR$^a$—OR$^b$, —N=C=O, —N=C=S, —NR$^a$—NR$^a$R$^b$, —NR$^a$C(O)NR$^a$N-R$^a$R$^b$, —NO, —N=C=NR$^a$, —S—CN, optionally substituted barbituric acid, optionally substituted thiobarbituric acid and —CH=CHR$^c$, wherein R$^a$ and R$^b$ are each independently selected from the group consisting of —H, alkyl, aryl, arylalkyl, cycloalkyl, heteroalkyl and haloalkyl or optionally R$^a$ and R$^b$ when attached to the same nitrogen atom are combined to form a 5-or 6-membered ring having from 0-2 additional heteroatoms as ring members selected from O, N and S, and wherein R$^c$ is selected from the group consisting of —OR$^{c1}$, —OC(O)R$^{c1}$, CO$_2$R$^{c1}$, —NR$^{c1}$R$^{c2}$, —NR$^{c1}$C(O)R$^{c1}$, aryl, optionally substituted barbituric acid, optionally substituted thiobarbituric acid, wherein each of R$^{c1}$ and R$^{c2}$ is independently selected from the group consisting of $C_{1-8}$alkyl and aryl, or optionally R$^{c1}$ and R$^{c2}$ when attached to the same nitrogen atom are combined to form a 5-or 6-membered ring having from 0-2 additional heteroatoms as ring members selected from O, N and S; wherein each of $R^a$, $R^b$ and $R^c$ is optionally substituted with from 1-3 $C_{1-8}$alkoxy, $C_{1-8}$alkylamino or di($C_{1-8}$alkyl)amino;

$R^3$ is —H or $C_{1-8}$alkyl;

each $R^4$ is independently $C_{1-8}$alkyl;

the subscript n is an integer from 0-4;

the subscript m is an integer from 1-5;

the subscript p is 1 or 2; and the subscript q is an integer from 0-4.

In another aspect, the present invention provides a method of preparing a compound of formula I. The method includes contacting a compound of formula II:

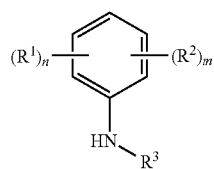

II with a compound of formula III:

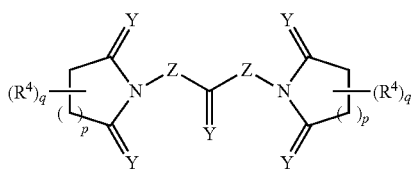

III under conditions sufficient to form a compound of formula I. The substituents $R^1$, $R^2$, $R^3$, $R^4$, Y and Z and the subscripts p and q are as defined above.

In yet another aspect, the present invention provides a method of rapid fluorescent labeling of N-glycans for analysis. The method includes contacting a dye compound having an N-hydroxysuccinimide carbamate moiety with N-glycans, in their glycosylamine form, under conditions sufficient to form labeled N-glycans. In some embodiments, the method includes contacting a compound of formula (I) with N-glycans, in their glycosylamine form, under conditions sufficient to form N-glycans labeled with a moiety (M):

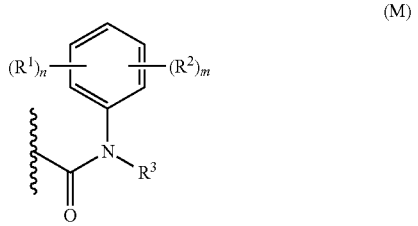

(M)

wherein $R^1$, $R^2$, $R^3$, m and n are as defined above in formula (I) and the wavy line indicates the point of attachment to the rest of molecule.

In still another aspect, the present invention provides a method of analyzing N-glycans. The method includes i) contacting a dye compound having an N-hydroxysuccinimide carbamate moiety with N-glycans under conditions sufficient to form labeled N-glycans; ii) providing the labeled N-glycans to an analytical means; and iii) detecting a fluorescent signal from the labeled N-glycans. In some embodiments, the dye compound is a compound of formula I. In certain instances, the N-glycans are labeled with moiety (M).

DETAILED DESCRIPTION OF THE INVENTION

I. Definitions

Figure 1:
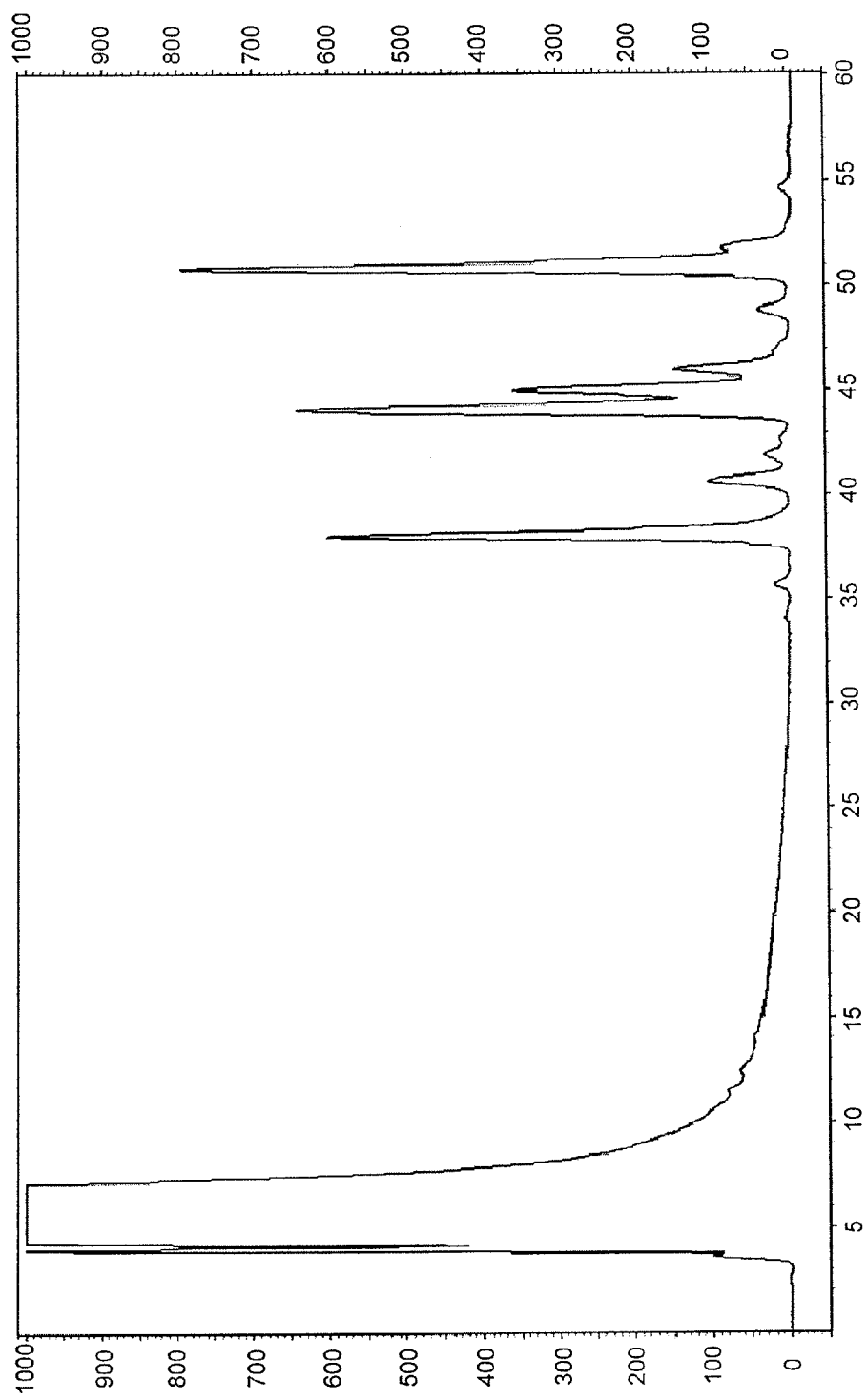
FIG. 1 shows the HPLC profile of fluorescent 4-AASC-labeled N-glycans from desialylated human polyclonal IgG.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the isomers. For each definitions herein (e.g., alkyl, alkoxy, haloalkyl, sulfoalkyl, phosphonoalkyl), when a prefix is not included to indicate the number of main chain carbon atoms in an alkyl portion, the radical or portion thereof will have eight or fewer main chain carbon atoms.

The term "cycloalkyl" refers to hydrocarbon rings having the indicated number of ring atoms (e.g., $C_{3-6}$cycloalkyl) and being fully saturated or having no more than one double bond between ring vertices. Cycloalkyl can be optionally substituted by one or more alkyls. One or two C atoms may optionally be replaced by a carbonyl. "Cycloalkyl" is also meant to refer to bicyclic and polycyclic hydrocarbon rings such as, for example, bicyclo [2.2.1]heptane, bicyclo [2.2.2]octane, etc.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR'R" is meant to include piperidinyl, pyrrolidinyl, morpholinyl, azetidinyl and the like.

The term "aryl" means, unless otherwise stated, a polyunsaturated, typically aromatic, hydrocarbon group, containing 6-12 ring atoms, which can be a single ring or multiple rings (up to three rings) which are fused together or linked covalently, wherein at least one of the fused rings comprising a bicyclic radical is aromatic. More specifically the term aryl includes, but is not limited to, phenyl, naphthyl, biphenyl, anthracenyl, phenanthrenyl, pyrenyl, indanyl (including, for example, indan-5-yl, or indan-2-yl, and the like) or tetrahydronapthyl (including, for example, tetrahydronapth-1-yl, or tetrahydronapth-2-yl, and the like), and the like.

The term "arylalkyl" means an alkyl radical, as defined herein, substituted with at least one, preferably one or two, aryl group(s) as defined herein, e.g., benzyl or phenethyl, and the like.

"Halo" means fluoro, chloro, bromo, and iodo, preferably fluoro or chloro.

"Haloalkyl" means an alkyl radical, as defined herein, substituted with at least one, preferably one to five halogen atoms, preferably fluorine or chlorine, including those substituted with different halogens, e.g., —CH$_2$Cl, —CF$_3$, —CHF$_2$, —CF$_2$CF$_3$, —CF(CH$_3$)$_3$, or —CHFCl, and the like.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —Si(CH$_3$)$_3$, and —CH$_2$—CH=N—OCH$_3$. Up to two heteroatoms may be consecutive, such as, for example, —CH$_2$—NH—OCH$_3$ and —CH$_2$—O—Si(CH$_3$)$_3$.

As used herein, the term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like.

As used herein, the term "optionally substituted barbituric acid" means a barbituric acid radical, wherein one or more nitrogen atoms are optionally substituted with alkyl, aryl, arylalkyl, cycloalkyl or haloalkyl as defined herein.

As used herein, the term "optionally substituted thiobarbituric acid" means a thiobarbituric acid radical, wherein one or more nitrogen atoms are optionally substituted with alkyl, aryl, arylalkyl, cycloalkyl or haloalkyl as defined herein.

As used herein, the term "glycan" means polysaccharide or oligosaccharide.

As used herein, the term "heteroatom" is meant to include oxygen (O), sulfur (S), nitrogen (N) and silicon (Si). The nitrogen and sulfur atoms can be optionally oxidized.

As used herein, the term "sulfo" means a sulfo group, —SO$_3$H, or its salts.

As used herein, the term "phosphono" means a phosphono group, —PO$_3$H$_2$ or its salts.

As used herein, the term "sulfoalkyl" means an alkyl group to which a sulfo group is boned, wherein the alkyl is boned to the molecule of interest. Non-limiting sulfoalkyl groups include sulfomethyl, sulfoethyl, sulfopropyl, sulfoisopropyl, sulfobutyl, sulfoisobutyl, sulfopentyl, sulfoisopentyl, sulfohexyl, sulfoisohexyl, sulfoheptyl, sulfooctyl, sulfoisooctyl and isomers thereof.

As used herein, the term "phosphnoalkyl" means an alkylgroup to which a phosphono group is boned, wherein the alkyl is boned to the molecule of interest. Non-limiting phosphonoalkyl groups include phosphonomethyl, phosphonoethyl, phosphonopropyl, phosphonoisopropyl, phosphonobutyl, phosphonoisobutyl, phosphonopentyl, phosphonoisopentyl, phosphonohexyl, phosphonoisohexyl, phosphonoheptyl, phosphonooctyl, phosphonoisooctyl and isomers thereof.

As used herein, the term "alkylsulfo" means a radical —S(O)$_2$(OR'), where R' is alkyl. Non-limiting alkylsulfo groups include methylsulfo, ethylsulfo, propylsulfo, isopropylsulfo, butylsulfo, isobutylsulfo, pentylsulfo, isopentylsulfo, hexylsulfo, isohexylsulfo, heptylsulfo, octylsulfo and isooctylsulfo and isomers thereof.

As used herein, the term "alkylphosphono" means a radical —P(O)(OR')(OR"), where R' and R" are alkyl or —H with the proviso that R' and R" are not both —H. Non-limiting alkylphosphono groups include methylphosphono, ethylphosphono, propylphosphono, isopropylphosphono, butylphosphono, isobutylphosphono, pentylphosphono, isopentylphosphono, hexylphosphono, isohexylphosphono, heptylphosphono, octylphosphono and isooctylphosphono and isomers thereof.

II. General

The present invention is related to compounds and methods for rapid labeling of N-glycans. The labels attached to glycans, such as N-glycans can be anything suitable for amino assays or other recognition assays, which include, but are not limited to, biotin, streptavidin, (histidine)$_6$ tag and small antigens easily recognized by antibodies. In one aspect, the present invention is directed to compounds and methods useful for rapid fluorescent labeling of N-glycans. Specifically, the present invention relates to fluorescent activated monocyclic aromatic carbamates or thiocarbamates that are capable of very rapidly fluorescent labeling of N-glycans in their glycosylamine form, under mild conditions and without the degradation of glycans during the labeling process. Advantageously, the compounds and methods of the present invention allow the fluorescent labeling of N-glycans to be carried out following enzymatic release of N-glycans both under native conditions or under denaturing conditions. In addition, the present invention provides high labeling efficiency. Labeling can be performed during the collection of released N-glycans, eliminating the drying and labeling incubation steps. Moreover, labeling reaction is rapid and completed within milliseconds or minutes. Labeling under mild conditions at higher pH further reduces the risk of desialylation. Higher fluorescence results in easier detection and better resolution.

III. Compounds

In one aspect, the present invention provides a compound of formula I:

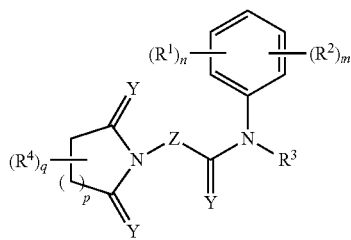

I

In one embodiment, the subscript p is 1. In another embodiment, p is 2. In yet another embodiment, q is 0. In a preferred embodiment, p is 1 and q is 0, Subscripts n and m are integers selected such that (m+n) is equal or less than 5.

For the compounds of the present invention, the molecular weight is typically less or equal to 1000. In some instances, the compounds have a molecular weight less or equal to 800. In some instances, preferred compounds have a molecular weight of less than 600, more preferably less than 500, even more preferably less than 450. In one group of preferred embodiments, the compounds have a molecular weight of from about 250 to about 450. The compounds can be monocyclic aromatics or fused multi-ring aromatics. The fused multi ring aromatic compounds can have 2, 3, or 4 fused carbocyclic aromatic rings. For improved resolution, the compounds are preferably monocyclic aromatics. The substituents are selected such that the compounds have certain solubility in water.

In formula I, Y is selected from oxygen or sulfur. Preferably, Y is oxygen.

In formula I, Z is oxygen or sulfur. Preferably, Z is oxygen. In another embodiment, Z is sulfur. In yet another embodiment, Y and Z are oxygen, p is 1 and q is 0.

In formula I and within any of the embodiments described herein, $R^1$ is selected from the group consisting of $C_{1-8}$alkyl, heteroalkyl and aryl, optionally, adjacent $R^1$ groups together with the atoms to which they are attached form a fused carbocyclic aromatic ring system having from 1-4 $R^5$ substituents selected from the group consisting of —COOH, —COO$^-$M$^+$, sulfo, alkylsulfo, phosphono and alkylphosphono. M$^+$ is selected from the group consisting of NH$_4^+$, Li$^+$, Na$^+$, K$^+$ and Cs$^+$. In some embodiments, the fused carbocyclic aromatic ring system has from 1-3 fused benzene rings. In other embodiments, the fused carbocyclic aromatic ring system is selected from the group consisting of naphthalene, phenanthrene, anthracene, triphenylene and pyrene. In one embodiment, $R^1$ is $C_{1-6}$alkyl, optionally substituted with from 1-3 members selected from —OR$^d$, —OC(O)OR$^d$, —OC(O)R$^d$, —OC(O)NR$^d$R$^e$, —SR$^d$, —S(O)R$^d$, —S(O)$_2$R$^d$, —S(O)$_2$NR$^d$R$^e$, —NR$^d$S(O)$_2$R$^e$, —C(O)NR$^d$R$^e$, —C(O)R$^d$, —C(=S)R$^d$, —NR$^d$C(O)R$^d$, —NR$^d$C(O)NR$^d$R$^e$, —CO$_2$R$^d$, —NR$^d$CO$_2$R$^e$, —CN, —NO$_2$, —N(R$^d$)$_2$, —NR$^d$S(O)NR$^d$R$^e$, —NR$^d$R$^e$C(=NR$^e$)NR$^d$R$^e$, —N$_3$, —NR$^d$—OR$^e$, —N=C=O, —N=C=S, —NR$^d$—NR$^d$R$^e$, —NR$^d$C(O)NR$^d$NR$^d$R$^e$, —NO, —N=C=NR$^d$ or —S—CN, wherein R$^c$, R$^d$ and R$^e$ are each independently $C_{1-8}$alkyl or aryl. In another embodiment, $R^1$ is $C_{1-8}$heteroalkyl.

In one embodiment, the aryl in $R^1$ is phenyl optionally substituted with from 1-3 members selected from the group consisting of $C_{1-8}$alkyl, —OR$^d$, —OC(O)OR$^d$, —OC(O)R$^d$, —OC(O)NR$^d$R$^e$, —SR$^d$, —S(O)R$^d$, —S(O)$_2$R$^d$, —S(O)$_2$NR$^d$R$^e$, —NR$^d$S(O)$_2$R$^e$, —C(O)NR$^d$R$^e$, —C(O)R$^d$, —C(=S)R$^d$, —NR$^d$C(O)R$^d$, —NR$^d$C(O)NR$^d$R$^e$, —CO$_2$R$^d$, —NR$^d$CO$_2$R$^e$, —CN, —NO$_2$, —N(R$^d$)$_2$, —NR$^d$S(O)NR$^d$R$^e$, —NR$^d$R$^e$C(=NR$^e$)NR$^d$R$^e$, —N$_3$, —NR$^d$—OR$^e$, —N=C=O, —N=C=S, —NR$^d$—NR$^d$R$^e$, —NR$^d$C(O)NR$^d$NR$^d$R$^e$, —NO, —N=C=NR$^d$ and —S—CN.

In formula I and within any of the embodiments described herein, each $R^2$ is independently selected from the group consisting of aryl, heteroaryl, —OR$^a$, —OC(O)OR$^a$, —OC(O)R$^a$, —OC(O)NR$^a$R$^b$, —SR$^a$, —S(O)R$^a$, —S(O)$_2$R$^a$, —S(O)$_2$NR$^a$R$^b$, —NR$^a$S(O)$_2$R$^b$, —C(O)NR$^a$R$^b$, —C(O)R$^a$, —C(=S)R$^a$, —NR$^a$C(O)R$^a$, —NR$^a$C(O)NR$^a$R$^b$, —CO$_2$R$^a$, —COO$^-$M$^+$, —NR$^a$CO$_2$R$^b$, —CN, —NO$_2$, —N(R$^a$)$_2$, —NR$^a$S(O)NR$^a$R$^b$, —NR$^a$R$^b$C(=NR$^b$)NR$^a$R$^b$, —N$_3$, —NR$^a$—OR$^b$, —N=C=O, —N=C=S, —NR$^a$—NR$^a$R$^b$, —NR$^a$C(O)NR$^a$NR$^a$R$^b$, —NO, —N=C=NR$^a$, —S—CN, sulfo, sulfoalkyl, phosphono, alkylphosphono, phosphonoalkyl and alkylsulfo, optionally substituted barbituric acid, optionally substituted thiobarbituric acid and —CH=CHR$^c$, wherein R$^a$ and R$^b$ are each independently selected from the group consisting of —H, alkyl, aryl, arylalkyl, cycloalkyl, heteroalkyl and haloalkyl or optionally R$^a$ and R$^b$ when attached to the same nitrogen atom are combined to form a 4-6 membered ring having from 0-2 additional heteroatoms as ring members selected from O, N and S, and wherein R$^c$ is selected from the group consisting of halo, haloalkyl, —OR$^{c1}$, —OC(O)R$^{c1}$, CO$_2$R$^{c1}$, —NR$^{c1}$R$^{c2}$, —NR$^{c1}$C(O)R$^{c1}$, aryl, optionally substituted barbituric acid, optionally substituted thiobarbituric acid, wherein each of R$^{c1}$ and R$^{c2}$ is independently selected from the group consisting of $C_{1-8}$alkyl and aryl, or optionally R$^{c1}$ and R$^{c2}$ when attached to the same nitrogen atom are combined to form a 4-6 membered ring having from 0-2 additional heteroatoms as ring members selected from O, N and S; wherein each of R$^a$, R$^b$ and R$^c$ is optionally substituted with from 1-3 $C_{1-8}$alkoxy, $C_{1-8}$alkylamino or di($C_{1-8}$alkyl)amino. In one embodiment, each of R$^a$ and R$^b$ is independently —H, $C_{1-8}$alkyl, $C_{1-8}$heteroalkyl, aryl, ary-$C_{1-8}$alkyl, $C_{3-6}$cycloalkyl and $C_{1-4}$haloalkyl, optionally substituted with from 1-3 $C_{1-8}$alkoxy, $C_{1-8}$alkylamino or di($C_{1-8}$alkyl)amino. In one instance, the $C_{1-8}$heteroalkyl is $C_{1-8}$alkyl substituted with from 1-3-OR$^d$, —OC(O)OR$^d$, —OC(O)R$^d$, —OC(O)NR$^d$R$^e$, —SR$^d$, —S(O)R$^d$, —S(O)$_2$R$^d$, —S(O)$_2$NR$^d$R$^e$, —NR$^d$S(O)$_2$R$^e$, —C(O)NR$^d$R$^e$, —C(O)R$^d$, —C(=S)R$^d$, —NR$^d$C(O)R$^d$, —NR$^d$C(O)NR$^d$R$^e$, —CO$_2$R$^d$, —NR$^d$CO$_2$R$^e$, —CN, —NO$_2$, —N(R$^d$)$_2$, —NR$^d$S(O)NR$^d$R$^e$, —NR$^d$R$^e$C(=NR$^e$)NR$^d$R$^e$, —N$_3$, —NR$^d$—OR$^e$, —N=C=O, —N=C=S, —NR$^d$—NR$^d$R$^e$, —NR$^d$C(O)NR$^d$NR$^d$R$^e$, —NO, —N=C=NR$^d$ and —S—CN. In some embodiments, R$^c$, R$^d$ and R$^e$ are each independently $C_{1-8}$alkyl or aryl.

In one group of embodiments of compounds having formula I and within any of the embodiments described herein, $R^2$ is an electron donating group. Non-limiting examples of electronic donating groups include —OR$^a$, —OC(O)OR$^a$, —OC(O)R$^a$, —OC(O)NR$^a$R$^b$, —SR$^a$, —NR$^a$R$^b$, —NR$^a$—OR$^b$, —NR$^a$—C(O)OR$^b$, —NR$^a$C(O)R$^b$ and —NR$^a$R$^b$.

In another group of embodiments of compounds having formula I and within any of the embodiments described herein, R$^2$ is an electron withdrawing group. Non-limiting electronic withdrawing groups include —CO$_2$R$^a$, —CN, —NO$_2$, —N$_3$, —N=C=O, —N=C=S, —NO, —N=C=NR$^a$, —S(O)R$^a$, —S(O)$_2$R$^a$, —S(O)$_2$NR$^a$R$^b$, —C(O)NR$^a$R$^b$, —C(O)R$^a$, —C(O)SR$^a$, —C(S)OR$^a$, —C(=S)R$^a$, —S—CN, sulfo, phosphono, alkylphosphono and alkylsulfo. In certain instances, R$^2$ is selected from the group consisting of —CO$_2$R$^a$, —CONR$^a$R$^b$, sulfo and phosphono. For example, R$^2$ is —COOH, —CONH$_2$, —SO$_3$H or —PO$_3$H$_2$.

In yet another group of embodiments of compounds having formula I, R$^2$ is selected from —CH=CHR$^c$, optionally substituted barbituric acid and optionally substituted thiobarbituric acid. In one instance, R$^c$ is halo. In another instance, R$^c$ is C$_{1-8}$haloalkyl, for example, —CF$_3$.

In formula I, R$^3$ is —H or C$_{1-8}$alkyl. In a preferred embodiment, R$^3$ is —H. In another embodiment, R$^3$ is C$_{1-8}$alkyl, for example, —CH$_3$.

In formula I, each R$^4$ is independently C$_{1-8}$alkyl, subscript q is an integer from 0-4. Preferably, q is 0-2. More preferably, q is 0. In a preferred embodiment, p is 1 and q is 0.

Subformulae of Formula I.

In one group of embodiments, compounds of formula I have subformula Ia:

Ia

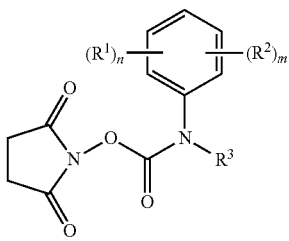

the substituents R$^1$, R$^2$ and R$^3$ and subscripts m and n are as defined above in the compounds of formula I and any of the embodiments of the compounds of formula I. In some embodiments of the compounds having formula (Ia), R$^3$ is —H.

In a second group of embodiments, compounds of formula I have subformula Ib:

Ib

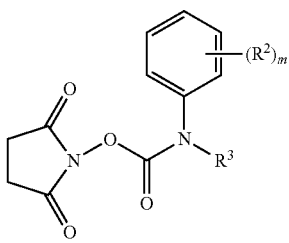

the substituents R$^2$ and R$^3$ and subscript m are as defined above in the compounds of formula I and any of the embodiments of the compounds of formula I. In some embodiments, R$^3$ is —H.

In a third group of embodiments, compounds of formula I have subformula Ic:

Ic

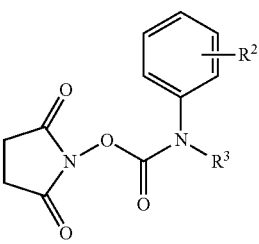

the substituents R$^2$ and R$^3$ are as defined above in the compounds of formula I and any of the embodiments of the compounds of formula I. In some embodiments, R$^3$ is —H.

In a fourth group of embodiments, compounds of formula I have subformula Id:

Id

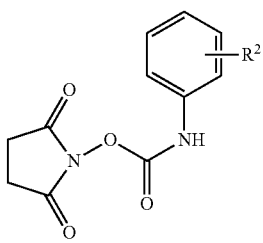

In certain instances, the present invention provides compounds having formula Id-1:

Id-1

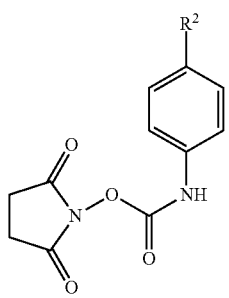

The substituent is as defined above in the compounds of formula I and any of the embodiments of the compounds of formula I. In some embodiments, the invention provides compounds having formula (Id-2):

Id-2

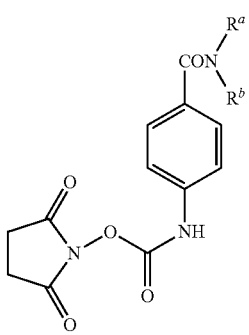

wherein $R^a$ and $R^b$ are each independently —H, $C_{1-8}$alkyl, aryl or aryl alkyl. In certain instances, $R^a$ and $R^b$ are —H.

In one embodiment, the compound of formula I has a subformula If-1 to If-3 and Ig-4 selected from:

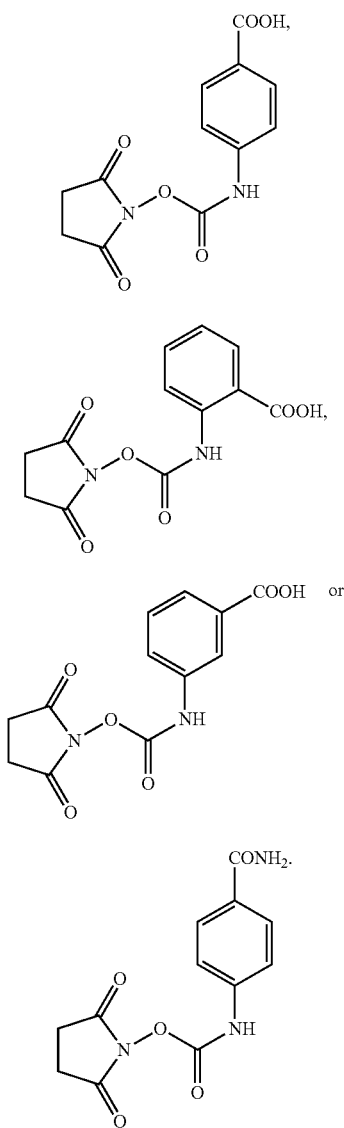

In a fifth group of embodiments, compounds of formula I have subformula Ie:

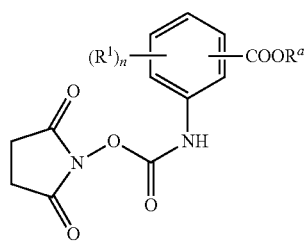

wherein the substituents $R^1$ and $R^a$ are defined above in the compounds of formula I and any of the embodiments of the compounds of formula I.

In a sixth group of embodiments, compounds of formula I have subformula Ig:

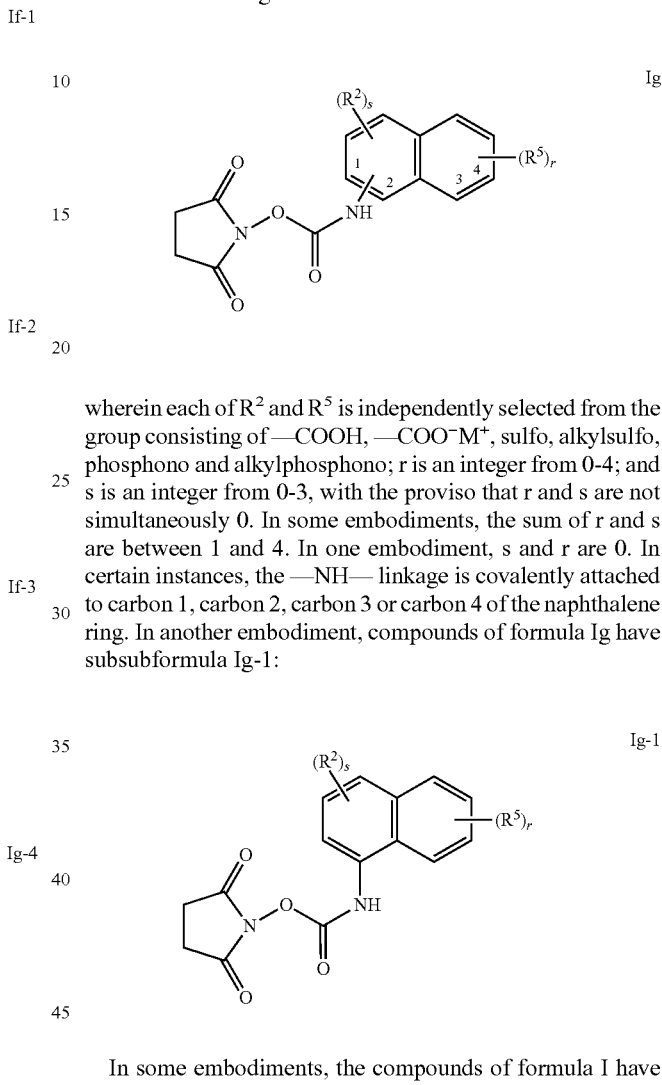

wherein each of $R^2$ and $R^5$ is independently selected from the group consisting of —COOH, —COO⁻M⁺, sulfo, alkylsulfo, phosphono and alkylphosphono; r is an integer from 0-4; and s is an integer from 0-3, with the proviso that r and s are not simultaneously 0. In some embodiments, the sum of r and s are between 1 and 4. In one embodiment, s and r are 0. In certain instances, the —NH— linkage is covalently attached to carbon 1, carbon 2, carbon 3 or carbon 4 of the naphthalene ring. In another embodiment, compounds of formula Ig have subsubformula Ig-1:

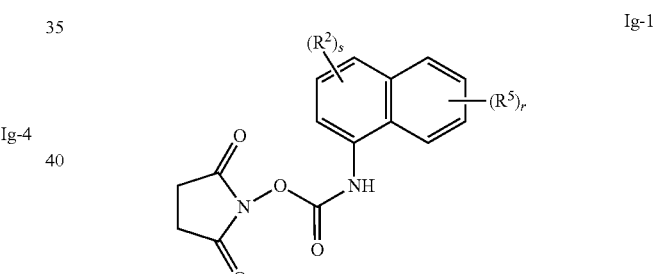

In some embodiments, the compounds of formula I have subformula Ig-2:

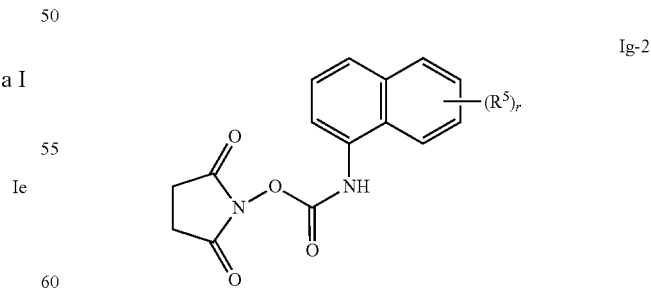

wherein $R^5$ and r are as defined above. In certain instances, r is 1 or 2 and $R^5$ is —COOH, —COO⁻M⁺, sulfo, alkylsulfo, phosphono or alkylphosphono, wherein M⁺ is H⁺, $NH_4^+$, Li⁺, Na⁺, K⁺ or Cs⁺. In other instances, r is 1 or 2 and $R^2$ is sulfo.

In some embodiments, the compounds of formula I have subformula Ig-3:

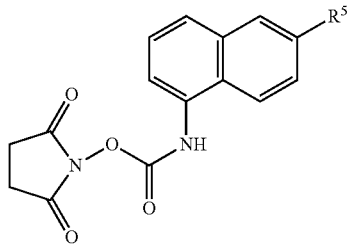

wherein s —COOH, —COO⁻M⁺, sulfo, alkylsulfo, phosphono or alkylphosphono, wherein $M^+$ is $H^+$, $NH_4^+$, $Li^+$, $Na^+$, $K^+$ or $Cs^+$. In certain instances, $R^5$ is —$SO_3M^+$, where $M^+$ is $H^+$, $NH_4^+$, $Li^+$, $Na^+$, $K^+$ or $Cs^+$.

In certain instances, compounds of formula Ig-1 are selected from the group consisting of:

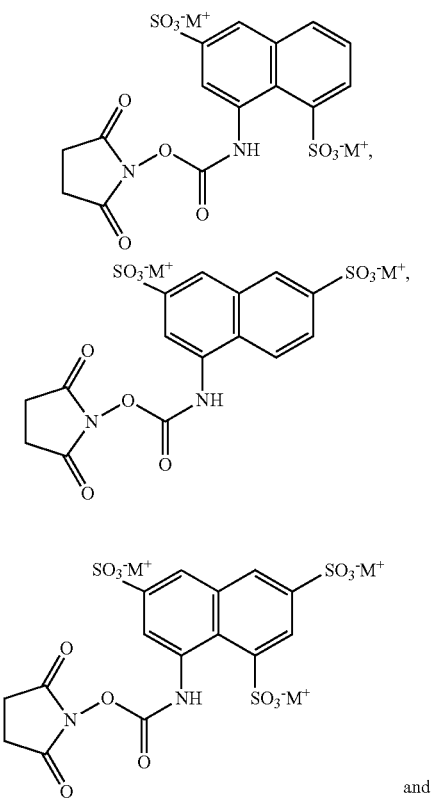

and

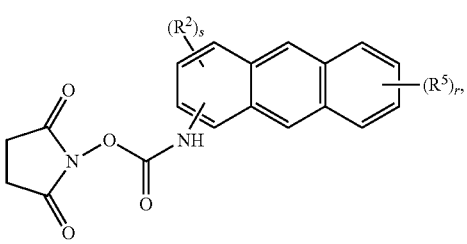

wherein $M^+$ is $H^+$, $NH_4^+$, $Li^+$, $Na^+$, $K^+$ or $Cs^+$.

In a seventh group of embodiments, compounds of formula I have subformula Ih:

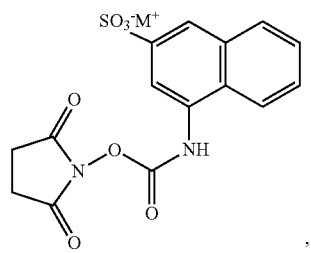

where each of $R^2$ and $R^5$ is independently selected from the group consisting of —COOH, —COO⁻M⁺, sulfo, alkylsulfo, phosphono and alkylphosphono; r is an integer from 0-4; and s is an integer from 0-3, with the proviso that r and s are not simultaneously 0. In one embodiment, the compounds of formula Ih have subformulae Ih-1 or Ih-2:

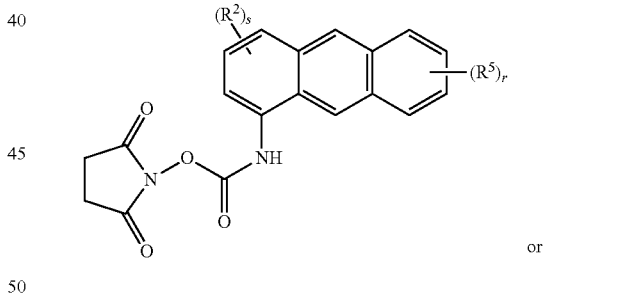

or

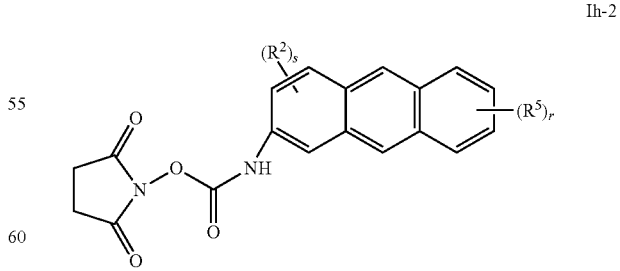

In certain instances, $R^2$ and $R^5$ are —COOH, —⁻M⁺, sulfo or phosphono, where $M^+$ is $NH_4^+$, $Li^+$, $Na^+$, $K^+$ or $Cs^+$. In one occurrence, $R^2$ and $R^5$ are sulfo.

In an eighth group of embodiments, compounds of formula I have subformula Ii:

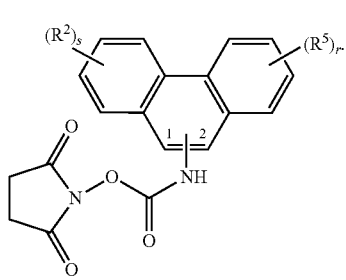

Ii where each of $R^2$ and $R^5$ is independently selected from the group consisting of —COOH, —COO$^-$M$^+$, sulfo, alkylsulfo, phosphono and alkylphosphono; r is an integer from 0-4; and s is an integer from 0-3, with the proviso that r and s are not simultaneously 0. In one embodiment, s and r are 0. In some embodiments, the sum of r and s is between 1 and 4. In another embodiment, r is 1, 2, 3 or 4; s is 1, 2 or 3; and $R^2$ and $R^5$ are a member selected from the group consisting of —COOH, —COO$^-$M$^+$, sulfo and phosphono. M$^+$ is NH$_4^+$, Li$^+$, Na$^+$, K$^+$ or Cs$^+$. In certain instances, the —NH— linkage is covalently attached to carbon 1 or carbon 2 of the aromatic ring.

In a ninth group of embodiments, compounds of formula I have subformula Ij:

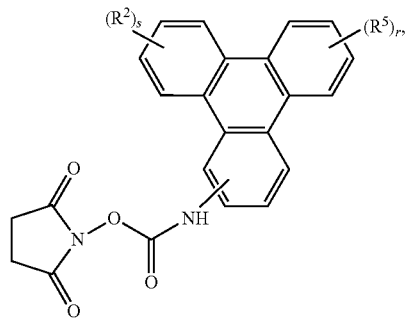

Ij where each of $R^2$ and $R^5$ is independently selected from the group consisting of —COOH, —COO$^-$M$^+$, sulfo, alkylsulfo, phosphono and alkylphosphono; r is an integer from 0-4; and s is an integer from 0-3, with the proviso that r and s are not simultaneously 0. In one embodiment, compounds of subformula Ij are selected from the group consisting of:

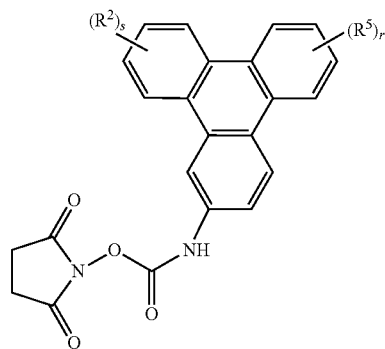

Ij-1 and

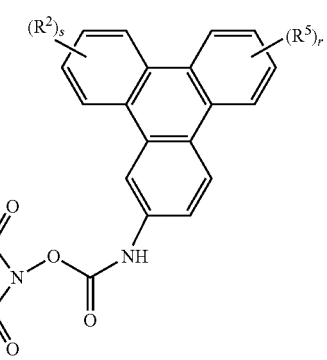

Ij-2

In certain instances, $R^2$ and $R^5$ are sulfo or phosphono.

In a tenth group of embodiments, compounds of formula I have subformula Ik:

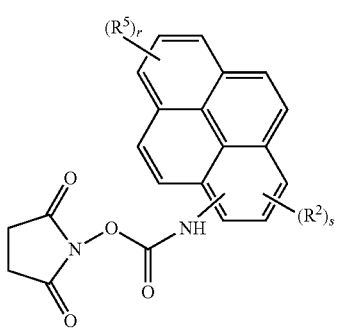

Ik here each of $R^2$ and $R^5$ is independently selected from the group consisting of —COOH, —COO$^-$M$^+$, sulfo, alkylsulfo, phosphono and alkylphosphono; r is an integer from 0-4; and s is an integer from 0-3, with the proviso that r and s are not simultaneously 0. In some embodiments, the sum of r and s is between 1 and 4. In one embodiment, the compounds of subformula Ik are selected from the group consisting of:

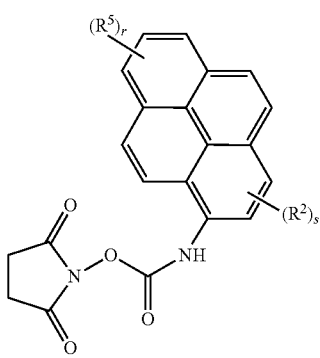

Ik-1 and

-continued

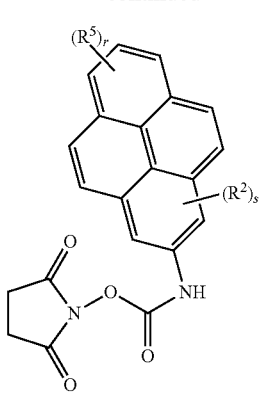

Ik-2

In certain instances, r=2, s=1. In certain other instances, $R^2$ and $R^5$ are sulfo groups. in yet certain other instances, r=2, s=1 and $R^2$ and $R^5$ are sulfo groups.

IV. Methods

In another aspect, the present invention provides a method of preparing compounds of formula I. The method includes contacting a compound of formula II:

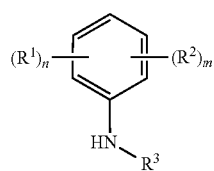

II with a compound of formula III:

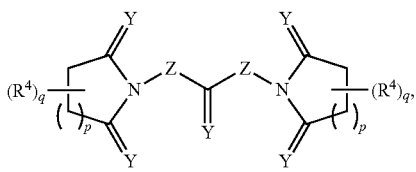

III wherein each Y is independently O= or S=;
Z is —O— or —S—;
each $R^1$ is independently selected from the group consisting of $C_{1-8}$alkyl, $C_{1-8}$heteroalkyl and aryl; optionally, adjacent $R^1$ groups together with the atoms to which they are attached form a fused carbocyclic aromatic ring system having from 1-4 $R^5$ substituents selected from the group consisting of —COOH, —COO⁻M⁺, sulfo, alkylsulfo, phosphono and alkylphosphono. In some embodiments, the fused carbocyclic aromatic ring system has from 1-3 additional fused benzene rings. In other embodiments, the fused carbocyclic aromatic ring system is selected from the group consisting of naphthalene, phenanthrene, anthracene, triphenylene and pyrene.
each $R^2$ is independently selected from the group consisting of aryl, heteroaryl, —OR$^a$, —OC(O)OR$^a$, —OC(O)R$^a$, —OC(O)NR$^a$R$^b$, —SR$^a$, —S(O)R$^a$, —S(O)$_2$R$^a$, —S(O)$_2$NR$^a$R$^b$, —NR$^a$S(O)$_2$R$^b$, —C(O)NR$^a$R$^b$, —C(O)R$^a$, —C(O)SR$^a$, —C(=S)R$^a$, —NR$^a$C(O)R$^a$, —NR$^a$C(O)NR$^a$R$^b$, —CO$_2$R$^a$, —COO⁻M⁺, —NR$^a$CO$_2$R$^b$, —CN, —NO$_2$, —N(R$^a$)$_2$, —NR$^a$S(O)NR$^a$R$^b$, —NR$^a$R$^b$C(=NR$^b$) NR$^a$R$^b$, —N$_3$, —NR$^a$—OR$^b$, —N=C=O, —N=C=S, —NR$^a$—NR$^a$R$^b$, —NR$^a$C(O)NR$^a$NR$^a$R$^b$, —NO, —N=C=NR$^a$, —S—CN, sulfo, alkylsulfo, sulfoalkyl, phosphono, alkylphosphono, phosphonoalkyl, optionally substituted barbituric acid, optionally substituted thiobarbituric acid and —CH=CHR$^c$, wherein R$^a$ and R$^b$ are each independently selected from the group consisting of —H, alkyl, aryl, arylalkyl, cycloalkyl, heteroalkyl and haloalkyl or optionally R$^a$ and R$^b$ when attached to the same nitrogen atom are combined to form a 4-6 membered ring having from 0-2 additional heteroatoms as ring members selected from O, N and S, and wherein R$^c$ is selected from the group consisting of —OR$^{c1}$, —OC(O)R$^{c1}$, CO$_2$R$^{c1}$, —NR$^{c1}$R$^{c2}$, —NR$^{c1}$C(O) R$^{c1}$, aryl, optionally substituted barbituric acid, optionally substituted thiobarbituric acid, wherein each of R$^{c1}$ and R$^{c2}$ is independently selected from the group consisting of $C_{1-8}$alkyl and aryl, or optionally R$^{c1}$ and R$^{c2}$ when attached to the same nitrogen atom are combined to form a 4-6 membered ring having from 0-2 additional heteroatoms as ring members selected from O, N and S; wherein each of R$^a$, R$^b$ and R$^c$ is optionally substituted with from 1-3 $C_{1-8}$alkoxy, $C_{1-8}$alkylamino or di($C_{1-8}$alkyl)amino; M⁺ is selected from the group consisting of NH$_4^+$, Li⁺, Na⁺, K⁺ and Cs⁺.

$R^3$ is —H or $C_{1-8}$alkyl;
each $R^4$ is independently $C_{1-8}$alkyl;
the subscript n is an integer from 0-4;
the subscript m is an integer from 1-5;
the subscript p is 1 or 2; and
the subscript q is an integer from 0-4. In one embodiment, the method further comprising: isolating the compounds of formula I. In some preferred embodiments, q is 0, p is 1, Y is =O, Z is —O—, and $R^3$ is —H.

As shown in the examples below, there are a variety of synthetic routes by which a skilled artisan can prepare compounds and intermediates of the present invention. The scheme below provide certain synthetic routes that can be followed to access all the compounds of the present invention. Other routes or modification of the routes presented below would be readily apparent to a skilled artisan and within the scope of the present invention. Scheme 1 illustrates one approach for the synthesis of compounds of formula I.

Scheme 1

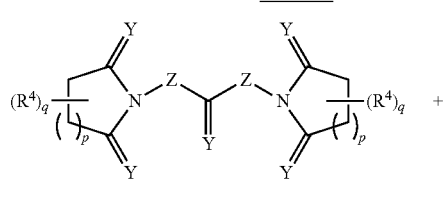

a

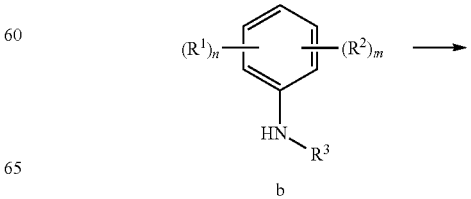

b

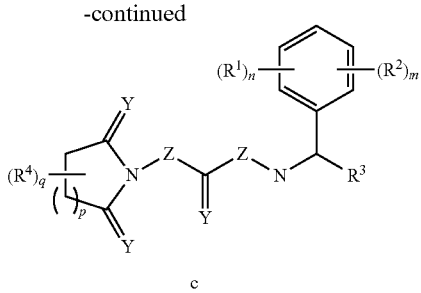

c

In one embodiment, various solvents can be used in the synthesis of compounds of formula I. Non-limiting examples of solvents include aprotic solvents, such as, acetonitrile, acetone, dimethyl sulfoxide (DMSO), dimethylformamide (DMF), THF, ether, dioxane; chlorinated solvents, such as dichloromethane, dichloroethane and chloroform; protic solvents, such as water, methanol, ethanol and isopropanol; hydrocarbon solvents, such as hexanes, petroleum ether, benzene, toluene and xylene. A mixture of the above solvents can also be used in the synthesis of compounds of formula I. Mixed solvents can have various ratios. For example, a two-components mixed solvents can have a volume ratio from about 1:10 to 10:1, such as 1:1, 1:2, 1:3, 1:4, 1:5, 1:6, 1:7, 1:8, 1:9 and 1:10. Preferably, the mixed solvents include solvents of different polarities.

The reactions can be carried out at various conditions. Preferably, the solvents used are anhydrous. Various ratios of reactants can be used. In one embodiment, the compounds of formula II and compounds of formula III are reacted in a molar ratio from about 1:5 to about 5:1, for example, 1:1, 1:2, 1:3, 1:4, 1:5, 2:1, 3:1, 4:1 and 5:1. For instance, compounds of formula II and compounds of formula III are reacted at a molar ratio of about 1:1. The reactants can have a concentration ranging from about 0.01 M to about 1 M, preferably from about 0.01 M to about 0.5 M. In some embodiments, the reaction is carried out at temperatures from about −20° C. to about 100° C., preferably, from 10° C. to about 100° C., more preferably from about 10° C. to about 85° C., even more preferably, from about 10° C. to about 60° C. In one embodiment, the reaction is carried out at about 22° C. In another embodiment, the reaction is carried out at about 80° C. In another instance, the reaction is carried out at the boiling point of the solvent, such as under refluxing condition. Preferably, the reactants are soluble in the solvents. In certain other embodiments, the reaction can also be carried out, where the reactants are in suspension. Starting material a in general is commercially available or can be prepared by reacting one equiv. of phosgene or methyl carbonate with excess of N-hydroxysuccinamide or N-hydroxythiosuccinamide. The substituted arylamine b can be synthesized by electrophilic substitution of a protected or unprotected aromatic amine using Friedel-Crafts acylation, sulfonation, phosphonation of aromatic compounds known in the art. Friedel-Crafts acylation reactions can be carried out by reacting an aromatic compound with carboxylic acids or anhydrides (see, Gore, *Chem. Ind.* (London) 1974, 727-731; Larock, *Comprehensive Organic Transformations*; VCH: New York, 1989, p 45-46; Olah, *Friedel-Crafts and Related Reactions*; Wiley: New York, 1963-1964, vol. 1, p 91-115; vol. 3, p 1-381; Lengyel, et al. *Synth. Comm.* 1998, 28, 1891). Sulfonation reaction can be carried out be reacting sulfuric acid with an aromatic compound using the procedures known in the art (see, Khelevin, *J. Org. Chem. USSR* 1984, 20, 339, 1173, 1723; 1987, 23, 1709; 1988, 24, 535; Gilbert, *Sulfonation and Related Reactions*; Wiley: NEw York, 1965, p 62-83, 87-124). Phosphonation reaction of aromatic compounds can be carried out by reacting phosphoric anhydride with an aromatic compound according to the procedures known in the art (see, *J. Am. Chem. Soc.;* 1954; 76(4) pp 1045-1051). The reaction is typically carried out at an elevated temperature.

The synthetic method of the present invention has several advantages, for example, the reactions are conducted under mild conditions, compatible with various functional groups and afford products in high yield. The method allows the facile synthesis of compounds of formula I having a variety of electronic donating and/or electronic withdrawing groups.

As shown in Scheme 2, the synthetic method above is also suitable for the synthesis of various dyes (f) containing N-hydroxysuccinimidyl carbamate moiety, where Dy represents a dye moiety. $NH_2$-Dy can be any dyes that are suitable for labeling and detecting glycans. Examples of these and other suitable dye classes can be found in Haugland, et al., HANDBOOK OF FLUORESCENT PROBES AND RESEARCH CHEMICALS, SIXTH ED., Molecular Probes, Eugene, Ore. 1996; U.S. Pat. Nos. 3,194,805; 3,128,179; 5,187,288; 5,188,934; 5,227,487; 5,248,782; 5,304,645; 5,433,896; 5,442,045; 5,556,959; 5,583,236; 5,808,044; 5,852,191; 5,986,086; 6,020,481; 6,162,931; 6,180,295; and 6,221,604; EP 1408366; Smith, et al., *J. Chem. Soc. Perkin Trans.* 2, 1993, 1195-1204; Whitaker, et al., *Anal. Biochem.* 207:267-279 (1992); Krasoviskii and Bolotin, ORGANIC LUMINESCENT MATERIALS, VCH Publishers, NY., 1988; Zolliger, COLOR CHEMISTRY, $2^{nd}$ Edition, VCH Publishers, NY., 1991; Hirschberg, et al., *Biochemistry* 37:10381-10385 (1998); Fieser and Fieser, REAGENTS FOR ORGANIC SYNTHESIS, Volumes 1 to 17, Wiley, US, 1995. Geiger, et al., *Nature* 359:859-861 (1992). Still other dyes are provided via online sites such as http://www.zeiss-.com. Exemplary dyes include but, are not limited to, monocyclic or fused carbocyclic aromatic compounds, monocyclic or fused heterocyclic aromatic compounds (e.g., amino substituted quinolines and acridines), xanthene dyes, coumarin dyes, dipyrromethenboron difluoride dyes and phenoxazine dyes, each of which contains one or more —$NH_2$ group.

Scheme 2

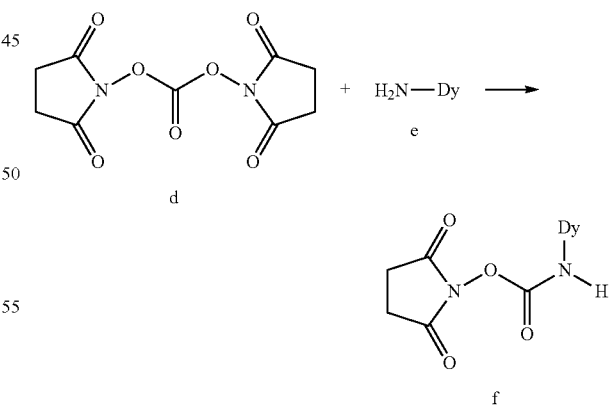

Dy—N-hydroxysuccinimidyl carbamate (f) can be prepared by reacting di(N-succinimidyl) carbonate d with a dye e under the reaction conditions as described above. Generally, dye e has a reactive amino group for reacting with di(N-succinimidyl) carbonate.

In another aspect, the present invention provides a method of rapid fluorescent labeling of N-glycan for analysis. The method includes contacting a dye of formula f (Scheme 2) with N-glycans under conditions sufficient to form N-glycans labeled with moiety —C(O)NH—Dy. The moiety Dy can be any dye that has a detectable fluorescent wavelength. The fluorescent emission of the dye can be in the UV, visible or infrared regions. For example, the fluorescent emission wavelength can be from about 200 nm to about 1000 nm. Preferably, the dye has a fluorescent emission wavelength from about 200-300, 300-350, 350-400, 400-500, 500-600, 600-800 or in the near IR region.

In yet another aspect, the present invention provides a method of rapid fluorescent labeling of N-glycans for analysis. The method includes contacting a compound of any of formulas I, Ia, Ib, Ic, Id, Id-1, Id-2, Ie, If-1, If-2, If-3, Ig, Ig-1, Ig-2, Ig-3, Ig-4, Ih, Ih-1, Ih-2, Ii, Ij-1, Ij-2, Ik, Ik-1 and Ik-2 with N-glycans under conditions sufficient to form N-glycans labeled with a moiety:

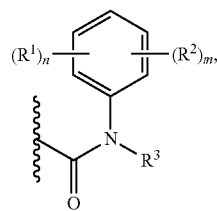

wherein $R^1$, $R^2$, $R^3$, m and n are as defined above and the wavy line indicates the point of attachment to the rest of the molecule.

In one embodiment, the N-glycans are released from the cleavage of glycoproteins by an enzyme. Various methods known in the art can be used to generate N-glycans from glycoprotein through deglycosylation processes. Examples of glycoproteins include, but are not limited to, antibodies and bovine fetuin (see, HPLC analysis in FIG. 1, FIG. 2 and FIG. 3). N-glycans can be either α-or β-glycosylamines. In one embodiment, the glycosylamine is aβ-glycosylamine having the formula:

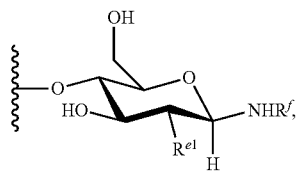

wherein $R^{e1}$ is —OH or —NHC(O)CH$_3$ and $R^f$ is —H or $C_{1-8}$alkyl. Preferably, $R^f$ is —H. The enzymes used in the present invention include, but are not limited to, peptide-N4-(acetyl-β-glucosaminyl)-asparagine amidase and PNGase F. In one embodiment, the reactions are carried out in the presence of detergents and/or reductants. Exemplary detergents include non-ionic detergent, sodium dodecyl sulfate, and non-ionic detergent Triton X-100. Exemplary reductants include β-meracaptoethanol. Alternatively, NaBH$_4$ and Pd/H$_2$ can be used.

The labeling reactions can be carried out at temperatures from about 0° C. to about 60° C., preferably, from about 10° C. to about 35° C., more preferably from about 15° C. to about 35° C., even more preferably from about 18° C. to about 30° C. In some preferred embodiments, the reaction is carried out at a temperature of about 5, 6, 7, 8, 9, 10, 11, 12, 13, 14, 15, 16, 17, 18, 19, 20, 21, 22, 23, 24, 25, 26, 27, 28, 29 or 30 degree Celsius.

The labeling reactions can be carried out in various environments. In one embodiment, the reactions are carried out in an aqueous solution. In another embodiment, the reaction can be carried out in an organic solvent or a mixture of solvents as defined above. In yet another embodiment, the reactions can be carried out in mixed solvents, such as a mixture of water and organic solvent in a predetermined ratio, for example, the mixed solvent can be water and a solvent as discussed above.

The labeling reactions can also be performed at a wide range of pH conditions. In one embodiment, the reactions are carried out at pH less than 7, for example, at pH from about 4 to about 7, such as a pH about 5, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9 or 7.0. In another embodiment, the reactions are carried out in a basic solution with pH greater than 7. In yet another embodiment, the reaction is carried out at a pH of 7.0. Preferably, the reaction is conducted at an elevated pH. The pH can be from about 7.1 to about 12, for example, at pH about 7.2, 7.3, 7.4, 7.5, 7.6, 7.7, 7.8, 7.9, 8.0, 8.1, 8.2, 8.3, 8.4, 8.5, 8.6, 8.7, 8.9, 9.0, 9.1, 9.3, 9.4, 9.5, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, or 12.

The labeling reactions are typically carried out by contacting the reactants from about 1 millisecond to about 15 minutes or 0.5 millisecond to about 10 minutes. In some embodiments, the reaction time is from about 0.5 ms to 1 ms, 1 ms to 10 ms, 10 ms to 50 ms, 50 ms to 100 ms, 100 ms to 200 ms, 200 ms to 500 ms, 500 ms to 1 s, 1 s to 5 s, 5 s to about 10 s, 10 s to 20 s, 20 s to 40 s, 40 s to 60 s, 60 s to 80 s, 80 s to 150 s, 150 s to 200 s, 200 s to 500 s, 500 s to 1 minute, 0.5 s to 15 minutes, and 0.5 minutes to about 10 minutes. In one embodiment, the reactions are completed in about 1 ms to about 10 minutes. In some instances, the reaction time is about 1, 2, 3, 4, 5, 6, 7, 8, 9, 10, 20, 30, 40, 50, 60, 70, 80, 90, 100, 200, 300, 400, 500, 600, 700, 800, 900, or 1000 ms. In other instances, the reaction time is about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 s. In yet other instances, the reaction time is about 0.5, 1, 2, 3, 4, 5, 6, 7, 8, 9 or 10 minutes.

The labeling method of the present invention allows the in situ labeling of N-glycans, for example, by contacting a compounds of any of formulas I, Ia, Ib, Ic, Id, Id-1, Id-2, Ie, If-1, If-2, If-3, Ig, Ig-1, Ig-2, Ig-3, Ig-4, Ih, Ih-1, Ih-2, Ii, Ij-1, Ij-2, Ik, Ik-1 and Ik-2 with N-glycans released from the glycoproteins. In one embodiment, labeling reactions can be carried out before, during or after the elution step, for example, released N-glycans are eluted directly into a collection plate containing aliquots of rapid labeling reagent containing a compounds of any of formulas I, Ia, Ib, Ic, Id, Id-1, Id-2, Ie, If-1, If-2, If-3, Ig, Ig-1, Ig-2, Ig-3, Ig-4, Ih, Ih-1, Ih-2, Ii, Ij-1, Ij-2, Ik, Ik-1 and Ik-2. As such, the present invention provides easy and efficient preparation of samples for analysis.

In still another aspect, the present invention provides a method of analyzing N-glycans. The method include i) contacting a compound of any of formulas I, Ia, Ib, Ic, Id, Id-1, Id-2, Ie, If-1, If-2, If-3, Ig, Ig-1, Ig-2, Ig-3, Ig-4, Ih, Ih-1, Ih-2, Ii, Ij-1, Ij-2, Ik, Ik-1 and Ik-2 with N-glycans under conditions sufficient to form labeled N-glycans, wherein the N-glycans are labeled with a moiety:

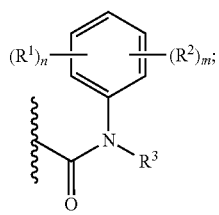

ii) providing the labeled N-glycans to an analytical means; and iii) detecting a fluorescent signal from the labeled N-glycans, wherein $R^1$, $R^2$, $R^3$, m and n are as defined above and the wavy line indicates the point of attachment to the rest of the molecule.

The analytical means can be any instrumentation that is suitable for detecting and analyzing labeled N-glycans. Typically, the analytical means include high-performance liquid chromatography (HPLC), capillary electrophoresis (CE), carbohydrate gel electrophoresis, microfluidic types of separation, mass spectrometry and the like. In one embodiment, liquid chromatography is used. The liquid chromatography techniques include, but are not limited to, normal phase or reverse phase high performance liquid chromatography, aqueous normal phase chromatography (also known as hydrophilic interaction chromatography), ion exchange chromatography, size exclusion chromatography, affinity chromatography and thin-layer chromatography. In one embodiment, the analytical means is HPLC. In yet another embodiment, the analytical means is capillary electrophoresis gel, microfluidic separation and mass spectrometry.

Typically, the compounds of the present invention are dissolved in a solvent and provided to an analytical means. The sample can be applied by injection or direct addition to an analytical means. For example, the samples can be added via a syringe. In one embodiment, the fluorescent signal emitted by the labeled N-glycans has a wavelength less than 400 nm. In another embodiment, the labeled N-glycans emit a signal having a wavelength in the range of 400-700 nm. In yet another embodiment, the labeled N-glycans emit a signal having a wavelength in the near infrared range, such as in the range of 700-1000 nm.

The use of fluorescent activated carbamates, such as compounds of formulas I, Ia, Ib, Ic, Id, Id-1, Id-2, Ie, If-1, If-2, If-3, Ig, Ig-1, Ig-2, Ig-3, Ig-4, Ih, Ih-1, Ih-2, Ii, Ij-1, Ij-2, Ik, Ik-1 or Ik-2, offers a number of significant advantages over other labeling processes based on reductive amination and other known methods of fluorescent labeling of glycosylamines. First, the present invention provides efficient sample preparation with minimized time of preparing samples for fluorescent labeling. Standard procedures for analyzing glycans released from glycoproteins require the glycans to be purified, often by multi-step procedures, from deglycosylated protein, buffers and reagents used during deglycosylation and thoroughly dried for several hours prior to labeling by reductive amination. In contrast, labeling using fluorescent activated carbamates can proceed in aqueous conditions and does not require the N-glycans to be purified or dried. Labeling can be performed directly on the whole sample, and the deglycosylation performed under native conditions or under denaturating conditions in the presence of detergents and/or reductants. Second, the present invention provides the facile labeling of N-glycans with minimized time required for labeling of N-glycans. For example, labeling based on reductive amination require incubation times ranging from ~1 hour to several hours (typically 2-3 hours). In comparison, labeling of N-glycans with fluorescent activated carbamates is completed within minutes. Third, the present invention provides labeled N-glycans with minimal degradation of the glycans during the fluorescent labeling process. Labeling procedures based on reductive amination typically require extended incubation times at elevated temperature and the presence of an acid catalyst. Depending on the specific reaction conditions, the labeling based on amination can result in a partial loss of sialic acid from sialylated glycans. Lower temperature and/or shorter incubation times minimize the possibility of desialylation, while higher temperature and longer incubation time favor higher labeling efficiency, but with increased desialylation. Typically, selected conditions of reductive amination represent a compromise between a high efficiency of labeling and a minimal desialylation. In contrast, labeling of N-glycans with fluorescent activated carbamates proceeds without any desialylation of sialylated glycans. Without wishing to be bound by theory, it is believed that the stability of N-glycans in the present labeling process is attributed to the use of very mild reaction conditions, including relatively mild changes in pH and low reaction temperatures, as well as the relatively short time over which the labeling reaction occurs compared to standard techniques. For example, the reaction is completed within minutes. Moreover, the present invention offers a great advantage over labeling processes based on reductive amination or labeling procedures in which the pH of the reaction becomes acidic upon labeling of glycans; for example, labeling of glycosylamines with FMOC-CL results in the generation of hydrochloric acid.

V. EXAMPLES

The following abbreviations are used in the Examples and throughout the description of the invention:

DMSO: dimethylsulfoxide

DMF: N,N-dimethylformamide

DMA: N,N-dimethylacetamide

4-AASC: 4-aminobenzoyl-N-hydroxysuccinimidyl carbamate

THF: tetrahydrofuran

APTS: 8-aminopyrene-1,3,6-trisulfonic acid

HPLC: high performance liquid chromatography

ANTS: 8-aminonaphthalene-1,3,6-trisulfonic acid

DSC: di(N-succinimidyl) carbonate

FMOC: fluorenylmethyoxycarbonyl

2-AB: 2-aminobenzamide

4-ABSC: 4-aminobenzamidyl-N-hydroxysuccinimidyl carbamate

APTSSC: 8-aminopyrene-1,3,6-trisulfonic acid-N-hydroxysuccinimidyl carbamate

ANTSSC: 8-aminonaphthalene-1,3,6-trisulfonic acid-N-hydroxysuccinimidyl carbamate ANSASC: 5-Amino-2-naphthalenesulfonic acid-N-hydroxysuccinimidyl carbamate The examples are for illustrative purposes and the invention is not limited to the examples disclosed.

Example 1

Synthesis of 4-aminobenzoyl-N-hydroxysuccinimidyl carbamate (4-AASC)

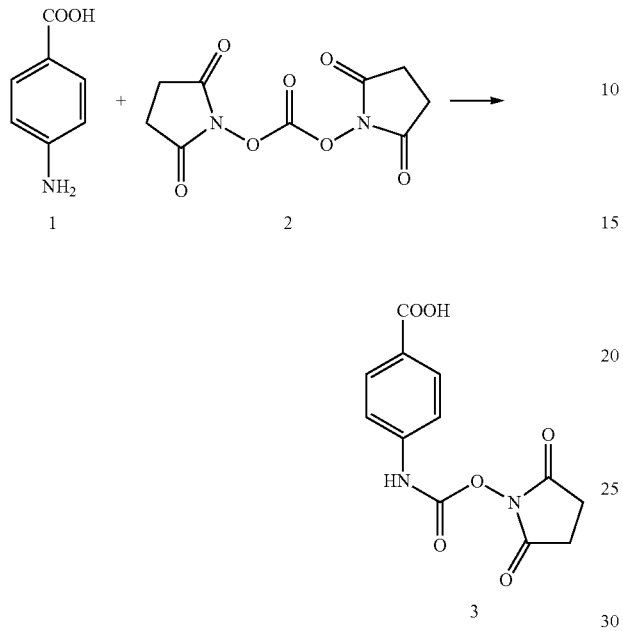

The example illustrates the synthesis of a derivative of 4-aminobenzoic acid, 4-aminobenzoyl-N-hydroxysuccinimidyl carbamate (3).

Compound 3 (4-AASC) was prepared based on a modified protocol developed for the synthesis of 6-aminoquinolyl-N-hydroxysuccinimidyl carbamate (Cohen et al. *Analytical Biochemistry* 211, 279-287, 1993). Di(N-succinimidyl) carbonate 2 (DSC, 6 mmol, 1.5 g) was dissolved in 50 ml of anhydrous acetonitrile and heated to reflux. 4-aminobenzoic acid 1 (4-AA, 5 mmol, 0.686 g) was dissolved in 25 ml of anhydrous acetonitrile and gradually added to the refluxing carbonate solution. The reaction was kept under reflux for 1 h. After 1 h, ~⅓ volume of acetonitrile was allowed to evaporate, the resulting solution was cooled to −20° C. and left for several days. The resulting precipitate was filtered and washed with cold acetonitrile. Compound 3 isolated (yield >85%) was dried in vacuum and stored in a desiccator at room temperature. H' NMR (DMSO-$d_6$): δ (ppm) 12.84 (1H, br), 11.19 (1H, s), 7.98 (2H, d), 7.59 (2H, d), 2.88 (4H, s).

Example 2

Synthesis of 3-aminobenzoyl-N-hydroxysuccinimidyl carbamate

Compound 3-aminobenzoyl-N-hydroxysuccinimidyl carbamate was prepared according to the procedures shown in Example 1 by reacting 3-aminobenzoic acid (CAS registry No.: 99-05-8) with di(N-succinimidyl) carbonate.

Example 3

Synthesis of 8-aminonaphthalene-1,3,6-trisulfonic acid-N-hydroxysuccimidyl carbamate

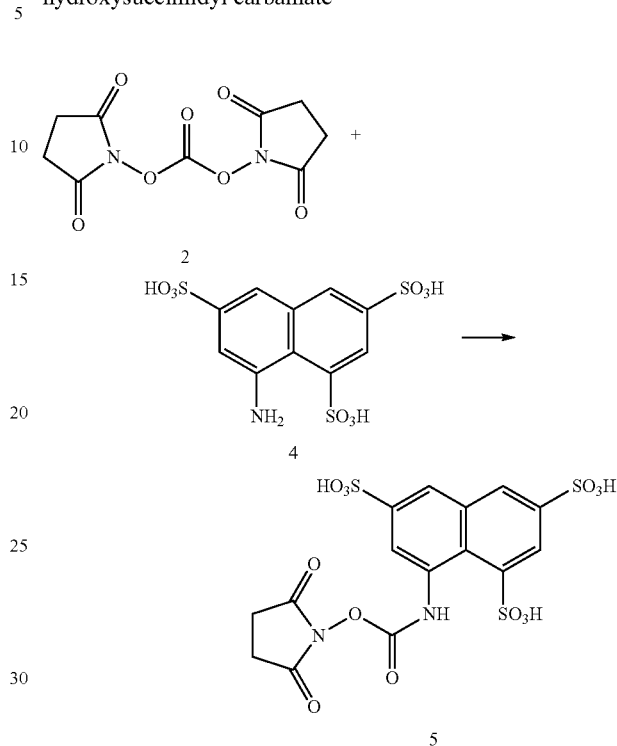

Compound 8-aminonaphthalene-1,3,6-trisulfonic acid-N-hydroxysuccimidyl carbamate (5) is prepared using the similar procedure as illustrated in Example 1. Di(N-succinimidyl) carbonate 2 (DSC, 6 mmol, 1.5 g) is dissolved in 50 ml of anhydrous acetonitrile and heated to reflux. 8-aminonaphthalene-1,3,6-trisulfonic acid 4 (ANTS, 5 mmol, 1.92 g) is dissolved in 30 ml of anhydrous acetonitrile and gradually added to the refluxing carbonate solution. The reaction is kept under reflux for 1 h. After 1 h, ~⅓ volume of acetonitrile is allowed to evaporate, the resulting solution is cooled to −20° C. and left for several days. The resulting precipitate is filtered and washed with cold acetonitrile. Compound 5 isolated is dried in vacuum and stored in a desiccator at room temperature. The yield is greater than 80%.

Example 4

Synthesis of 8-aminopyrene-1,3,6-trisulfonic acid-N-hydroxysuccimidyl carbamate (APTSSC)

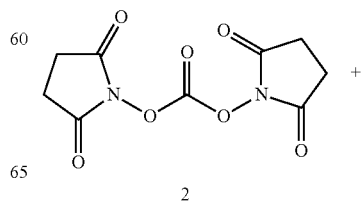

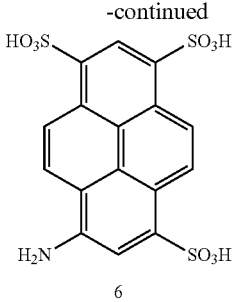

6

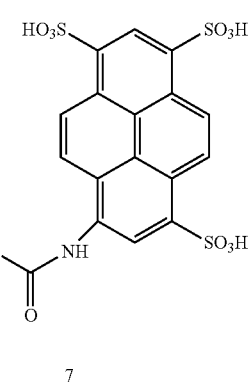

7

Compound 8-aminopyrene-1,3,6-trisulfonic acid-N-hydroxysuccimidyl carbamate (7) was prepared based on the similar illustrated in Example 1. Di(N-succinimidyl) carbonate 2 (DSC, 0.019 mmol, 10 mg) and 8-aminopyrene-1,3,6-trisulfonic acid 6 (APTS, 0.022 mmol, 5.7 mg) were dissolved in 2.5 ml of mixture containing 1 ml of anhydrous acetone, 1 ml of anhydrous DMF and 0.5 ml of anhydrous DMSO. The reaction was briefly sonicated and then stirred overnight at room temperature, in the dark. After overnight, the reaction mixture was concentrated to ~0.5 ml using vacuum centrifugal evaporator and aliquots were stored at −20° C. The reaction mixture containing crude APTS-N-hydroxysuccinimidyl carbamate was used for labeling experiments without further purification.

Example 5

Synthesis of 4-aminobenzamidyl-N-hydroxysuccinimidyl carbamate (4-ABSC)

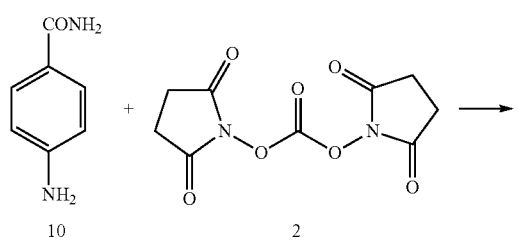

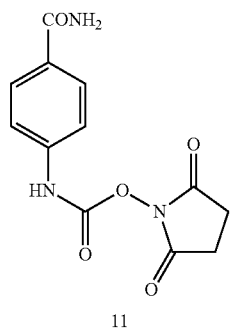

11

Compound II (4-ABSC) is prepared based on a modified protocol developed for the synthesis of 6-aminoquinolyl-N-hydroxysuccinimidyl carbamate (Cohen et al. *Analytical Biochemistry* 211, 279-287, 1993) and is synthesized according to the procedures of Example 1. Di(N-succinimidyl) carbonate 2 (DSC, 6 mmol, 1.5 g) is dissolved in 50 ml of anhydrous acetonitrile and heated to reflux. 4-aminobenzamide 10 (5 mmol, 0.681 g) is dissolved in 25 ml of anhydrous acetonitrile and gradually added to the refluxing carbonate solution. The reaction is kept under reflux for 1 h. After 1 h, ~⅓ volume of acetonitrile is allowed to evaporate, the resulting solution was cooled to −20° C. and left for several days. The resulting precipitate is filtered and washed with cold acetonitrile. Compound II isolated is dried in vacuum and stored in a desiccator at room temperature (yield >80%). H' NMR (DMSO-$d_6$): δ (ppm) 11.13 (1H, s), 7.87 (3H, m), 7.51 (2H, d), 7.33 (1H, s), 2.82 (4H, s).

Example 6

Synthesis of 5-Amino-2-naphthalenesulfonic acid-N-hydroxysuccinimidyl carbamate

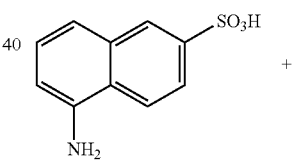

12

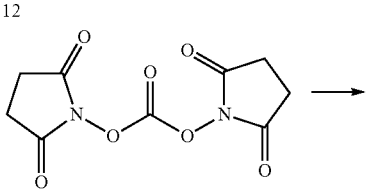

2

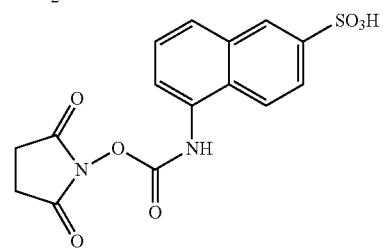

13

Compound 13 (ANSASC) is prepared based on a modified protocol developed for the synthesis of 6-aminoquinolyl-N- hydroxysuccinimidyl carbamate (Cohen et al. *Analytical Biochemistry* 211, 279-287, 1993) and is synthesized according to the procedures of Examples 1 and 6. Di(N-succinimidyl) carbonate 2 (DSC, 6 mmol, 1.5 g) is dissolved in 50 ml of anhydrous acetonitrile and heated to reflux. 5-Amino-2-naphthalenesulfonic acid 12 (5 mmol, 1.116 g) is dissolved in 30 ml of anhydrous acetonitrile and gradually added to the refluxing carbonate solution. The reaction is kept under reflux for 1 h. After 1 h, ~⅓ volume of acetonitrile is allowed to evaporate, the resulting solution is cooled to −20° C. and left for several days. The resulting precipitate is filtered and washed with cold acetonitrile. Compound 13 isolated is dried in vacuum and stored in a desiccator at room temperature (yield >80%). H' NMR (DMSO-$d_6$): δ (ppm) 9.15 (1H, s), 8.35 (1H, d), 7.63 (1H, m), 7.57 (1H, m), 7.38 (1H, m), 7.29 (1H, m), 6.98 (1H, d), 2.64 (4H, s), 2.0 (1H, s). $C^{13}$NMR (CDCL$_3$): δ (ppm) 169.0, 152.2, 141.0, 140.5, 133.2, 128.6, 126.4, 125.0, 123.2, 121.5, 119.8, 106.7, 25.6.

Example 7

Reaction of Compound 3 with D-Glycosylamines

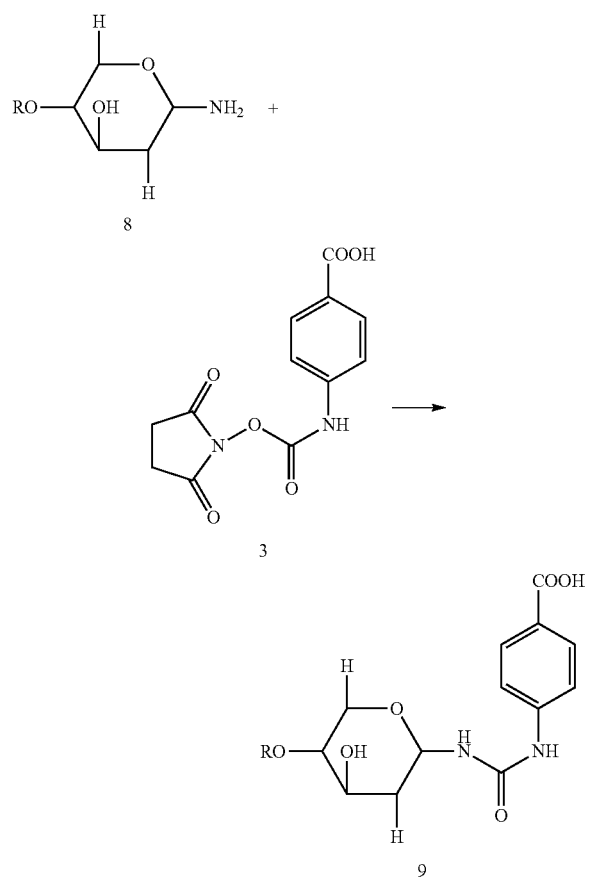

β-glycosylamine 8 was reacted with 4-aminobenzoyl-N-hydroxysuccinimidyl carbamate (4-AASC) 3. The reaction proceeded rapidly in an aqueous environment, at room temperature and the unreacted reagent rapidly decomposes to free 4-aminobenzoic acid, N-hydroxysuccinimide and carbon dioxide.

Example 8

Reaction of Compound 5 with β-Glycosylamines

β-glycosylamine 8 was reacted with 8-aminonaphthalene-1,3,6-trisulfonic acid-N-hydroxysuccimidyl carbamate (5). The reaction proceeded rapidly in an aqueous environment, at room temperature and the unreacted reagent rapidly decomposes to free 4-aminobenzoic acid, N-hydroxysuccinimide and carbon dioxide.

Example 9

Reaction of APTS-N-Hydroxysuccinimidyl Carbamate (7) with β-glycosylamines

Figure 3:
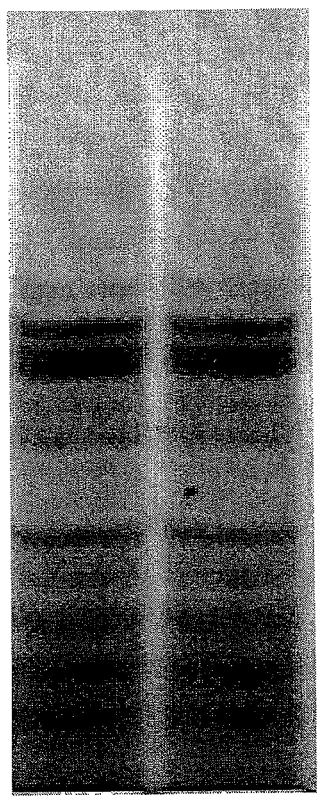
FIG. 3 shows the fluorophore-assisted gel electrophoresis (FACE) of fluorescent APTS-N-hydroxysuccinimidyl carbamate-labeled sialylated N-glycans from bovine fetuin.

Bovine fetuin (~100 µg, containing mainly negatively charged sialylated glycans) was deglycosylated at pH 8.6 under native conditions using PNGase F enzyme. Released glycosylamines (total volume ~50 W) were labeled using APTS-N-hydroxysuccinimidyl carbamate reagent (10 µl, ~5 minutes, room temperature). Aliquots of labeled sample were analyzed by fluorophore-assisted carbohydrate gel electrophoresis (FACE), using N-linked gel. FIG. 3 shows the gel profile of N-glycans in duplicate from bovine fetuin.

Example 10

Figure 2:
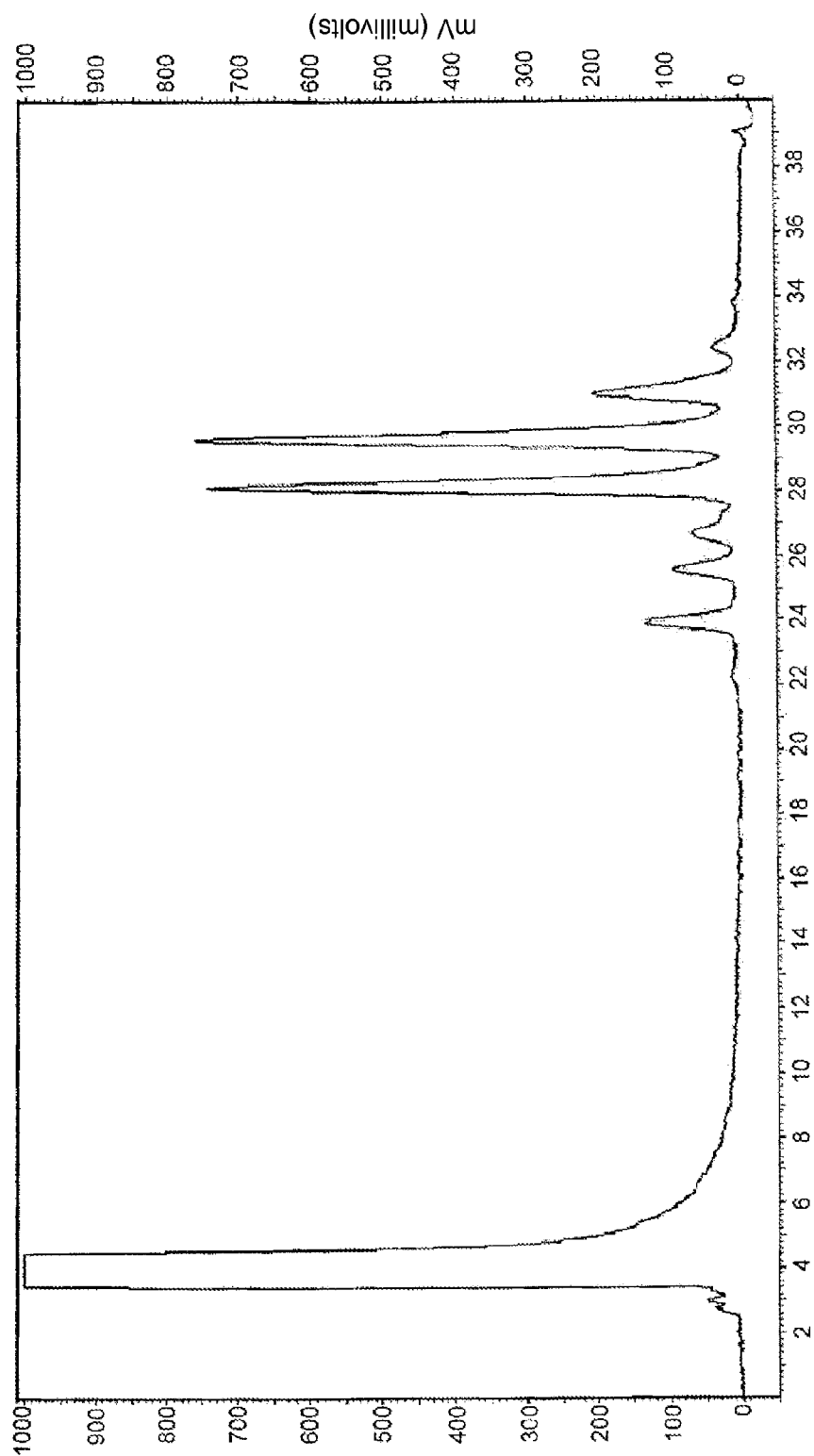
FIG. 2 shows the HPLC profile of fluorescent 4-AASC-labeled sialylated N-glycans from bovine fetuin.

4-AASC Labeling of N-Glycans Released from Test Glycoprotein Under Native and Denaturation Conditions Desialylated human polyclonal IgG (~100 µg, containing uncharged glycans) or of bovine fetuin (~100 µg, containing mainly negatively charged sialylated glycans) were deglycosylated at pH 8.6 under native conditions using PNGase F enzyme. Released glycosylamines were labeled using 4-AASC reagent (2-5 minutes, room temperature, ~10 mg 4-AASC/ml of acetonitrile) and directly analyzed by hydrophilic interaction chromatography on Glycosep N HPLC column. FIG. 1 shows HPLC profile of N-glycans from human IgG and FIG. 2 shows HPLC profile of N-glycans from bovine fetuin.

Example 11

Fluorescent Labeling of N-glycans using 4-aminobenzamidyl-N-hydroxysuccinimidyl carbamate (4-ABSC)

With the incorporation of rapid fluorescent labeling into enzymatic deglycosylation, a major rate-limiting step in glycan profiling can be potentially eliminated.

Rapid Labeling Protocol

Upon completion of enzymatic deglycosylation with PNGase F:
  Dissolve the rapid dye to a concentration of 50 mg/ml in a 25% DMF/75% acetonitrile solution (the Rapid Labeling Reagent).
  Released β-glycosylamines are eluted directly into a collection plate containing aliquots of Rapid Labeling Reagent.
  Post-labeling cleanup is performed.
  Samples are profiled by HPLC.

Rapid Labeling with 4-ABSC on β-Glycosylamines Enzymatically Released from Human Polyclonal IgG Human polyclonal IgG was enzymatically deglycosylated in 96-well microtiter plate format using PNGase F and the β-glycosylamines eluted into two separate microtiter plates. The first set of samples was eluted into an empty microtiter plate. Rapid labeling was performed by adding the Rapid Labeling Reagent to the samples by pipette using two different amounts. 5 µl was added to each well of one row and 10 µl to another. The second set of samples was eluted into a microtiter plate already containing 5 µl or 10 µl amounts of Rapid Labeling Reagent.

Figure 4:
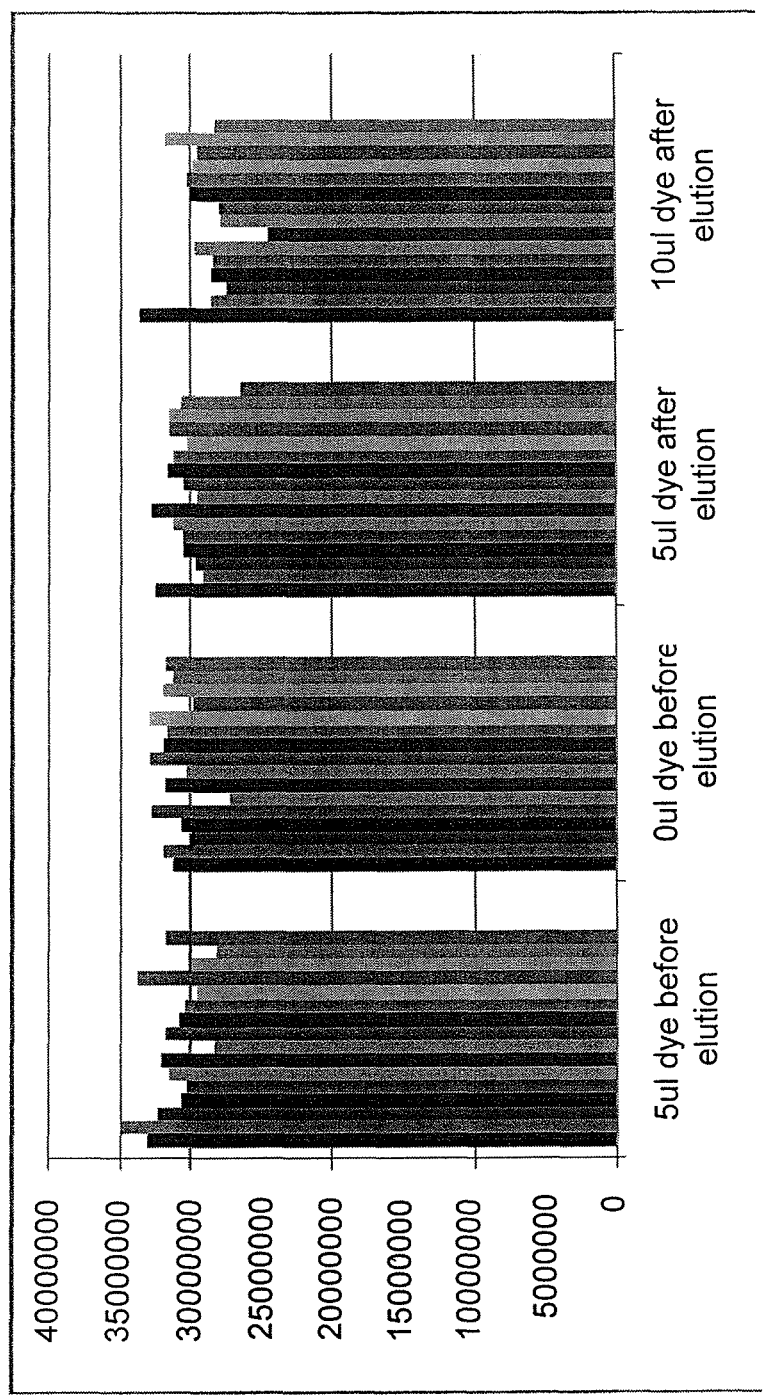
FIG. 4 shows results of comparison of rapid fluorescent labeling of N-glycans released from human polyclonal IgG, using 4-aminobenzamidyl-N-hydroxysuccinimidyl carbamate, (4-ABSC), where labeling was performed before or after elution of released N-glycans from 96-well deglycosylation microtiter plate.

After separation on the N-Plus Column, the total peak areas for both sets of samples and the two amounts of Labeling Reagent were plotted against each other as shown in FIG. 4. The results verified that rapid labeling during elution was as proficient as conventional labeling by pipette after elution. In addition, 5 ml of dye was shown to be sufficient for proper labeling.

Figure 5:
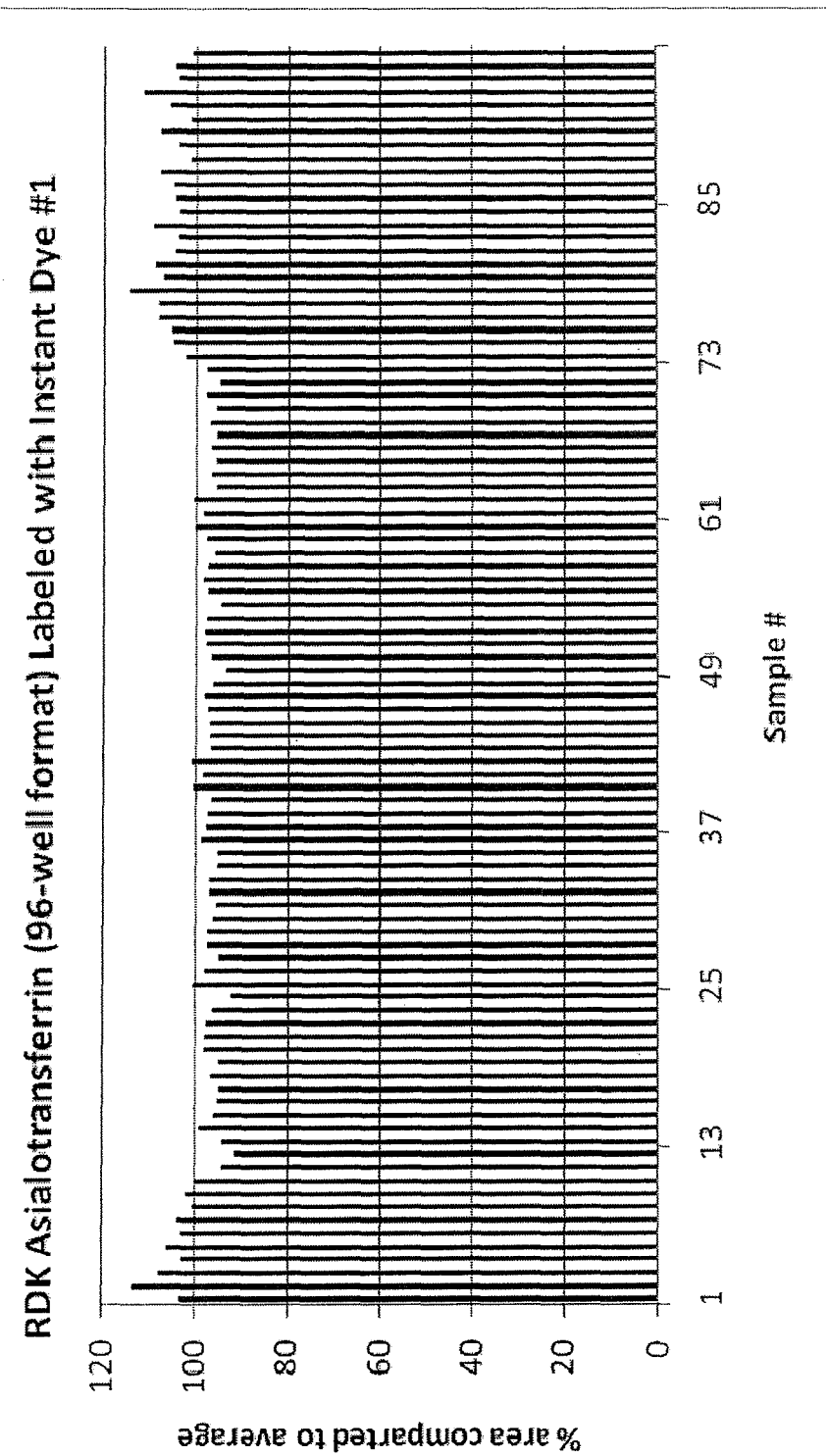
FIG. 5 shows a side-by-side comparison of the total peak area of the HPLC profiles of 4-aminobenzamidyl-N-hydroxysuccinimidyl carbamate (4-ABSC) labeled N-glycans released from multiple aliquots of Asialotransferrin using deglycosylation in a 96-well microtiter plate format.

Rapid Fluorescent Labeling Using 4-ABSC Performed on β-Glycosylamines Enzymatically Released from Asialotransferrin Asialotransferrin was enzymatically deglycosylated using PNGase F and the β-glycosylamines eluted into a microtiter plate containing 5 ul of the Rapid Labeling Reagent in each well. After separation on the N-Plus Column, the total peak areas for all the samples were plotted against each other as shown in FIG. 5. All areas were normalized to the average, represented as one hundred percent. The standard deviation is approximately 5%. The results verified reproducible labeling in a high-throughput sampling format.

Example 12

Figure 6:
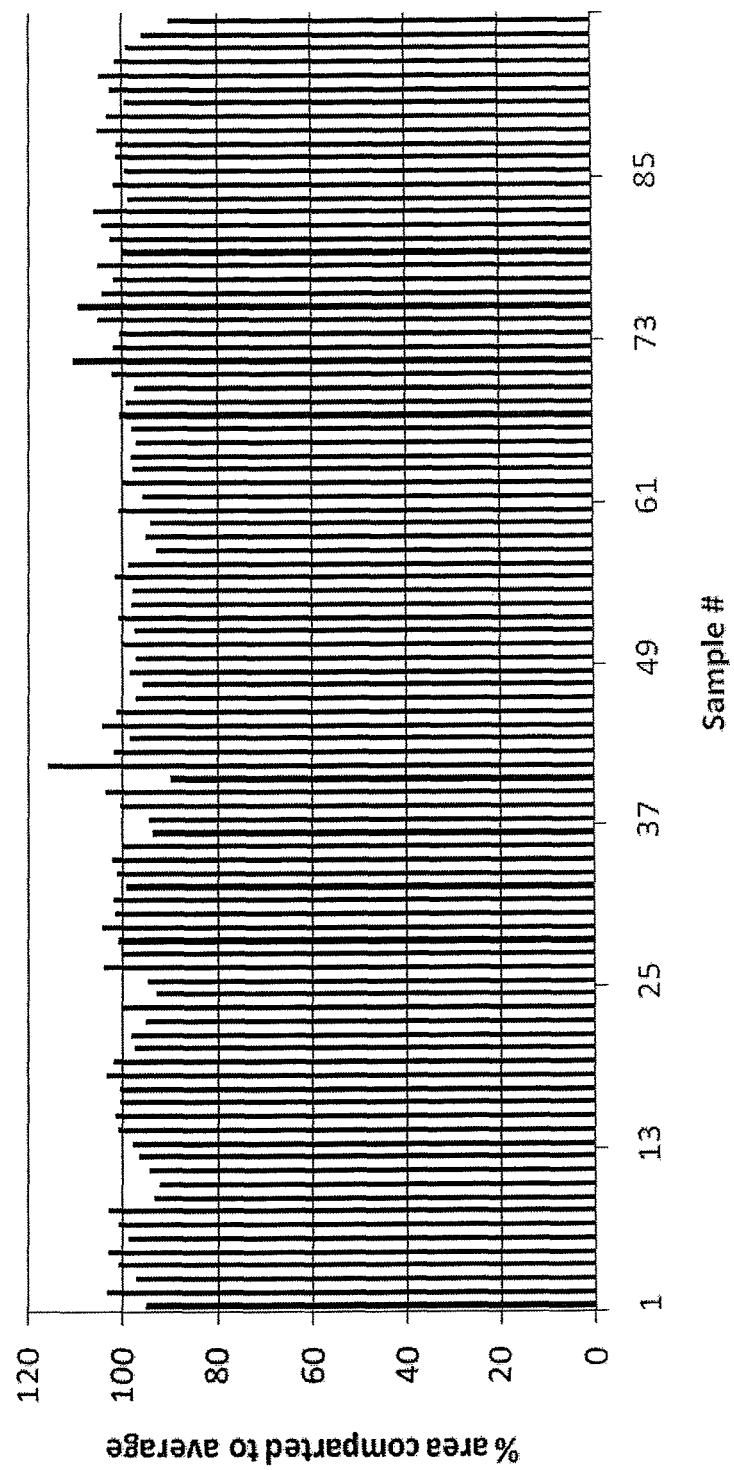
FIG. 6 shows a side-by-side comparison of the total peak area of the HPLC profiles of 4-aminobenzoyl-N-hydroxyusuccinimidyl carbamate (4-AASC) labeled N-glycans released from multiple aliquots of Asialotransferrin using deglycosylation in a 96-well microtiter plate format.

Rapid Fluorescent Labeling Using 4-Aminobenzoyl-N-Hydroxysuccinimidyl Carbamate (4-AASC) on β-Glycosylamines Enzymatically Released from Asialotransferrin Asialotransferrin was enzymatically deglycosylated using PNGase F and the β-glycosylamines eluted into a microtiter plate containing 5 ul of the Rapid Labeling Reagent in each well. After separation on the N-Plus Column, the total peak areas for all the samples were plotted against each other as shown in FIG. 6. All areas were normalized to the average, represented as one hundred percent. The standard deviation is approximately 5%. The results verified reproducible labeling in a high-throughput sampling format.

Example 13

Figure 7:
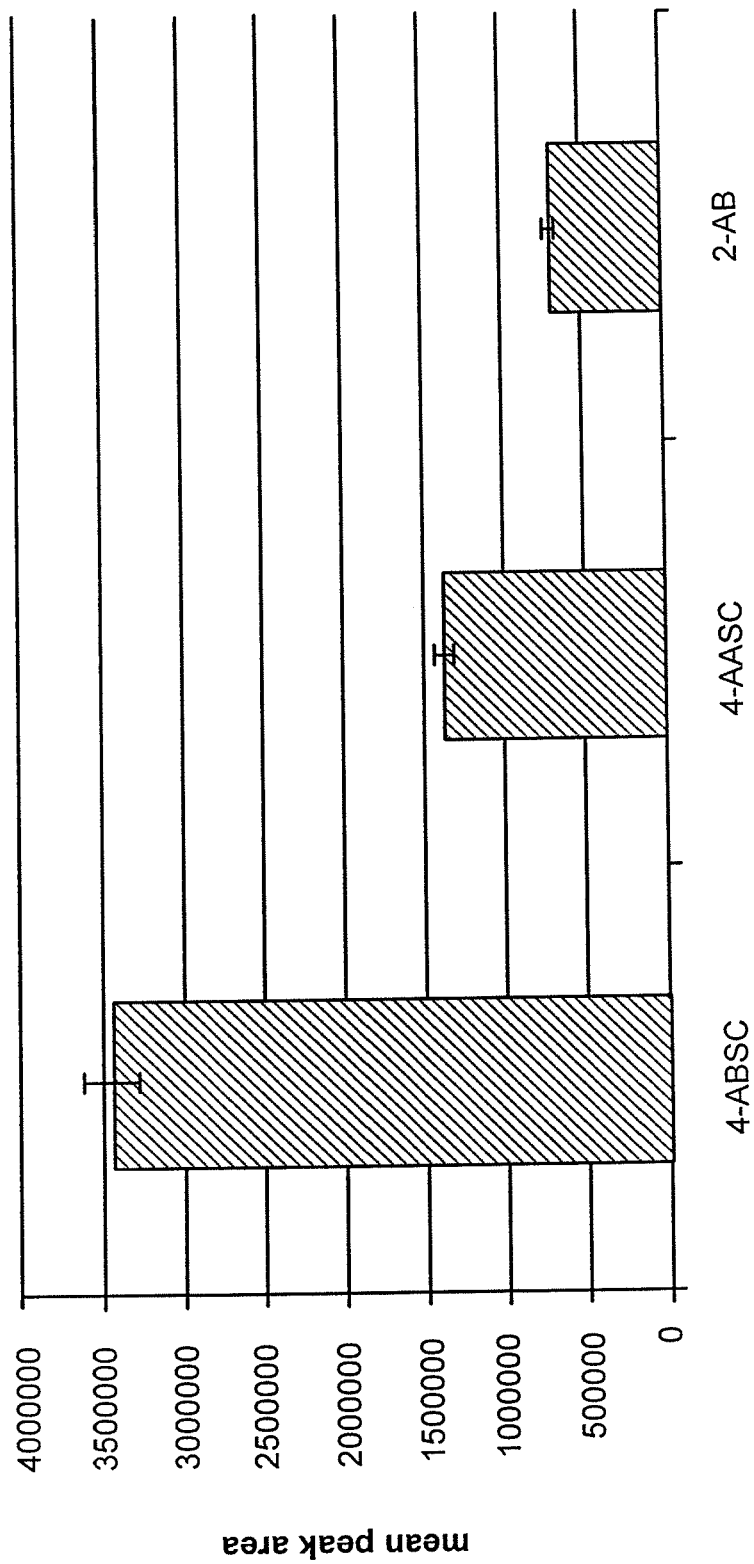
FIG. 7 shows a comparison of the average peak areas of the profiles of N-glycans labeled with 2-aminobenzamide (2-AB), 4-aminobenzamidyl-N-hydroxysuccinimidyl carbamate (4-ABSC) or 4-aminobenzoyl-N-hydroxysuccinimidyl carbamate (4-AASC).

Comparison of Fluorescence Signals of N-Glycans Labeled with 4-ABSC, 4-AASC and 2-AB Equivalent amounts of N-glycans were labeled either with 2-AB using reductive amination protocol or with 4-ABSC or 4-AASC using rapid labeling protocol. After clean up of N-glycans from the excess of a dye, equivalent aliquots of N-glycans were analyzed by HILIC HPLC with fluorescence detection (using excitation and emission wavelengths suitable for given dye) and N-glycan peak areas were compared. As shown in FIG. 7, rapid dye 4-ABSC achieved almost 2.5 times more signal than rapid dye 4-AASC. Both of the dyes showed stronger detection than that of the 2-AB labeled N-glycans, an art-recognized method used in glycan profiling. Although rapid dye 4-AASC is lower in terms of fluorescence, the dye is negatively charged. Neutral N-Glycans labeled with rapid dye 4-AASC have the advantage of being analyzed in the negative mode at the same time as sialylated N-glycans by MALDI.

Example 14

Comparison of HPLC Profiles of 4-AASC and 4-ABSC Labeled N-glycans

Figure 8:
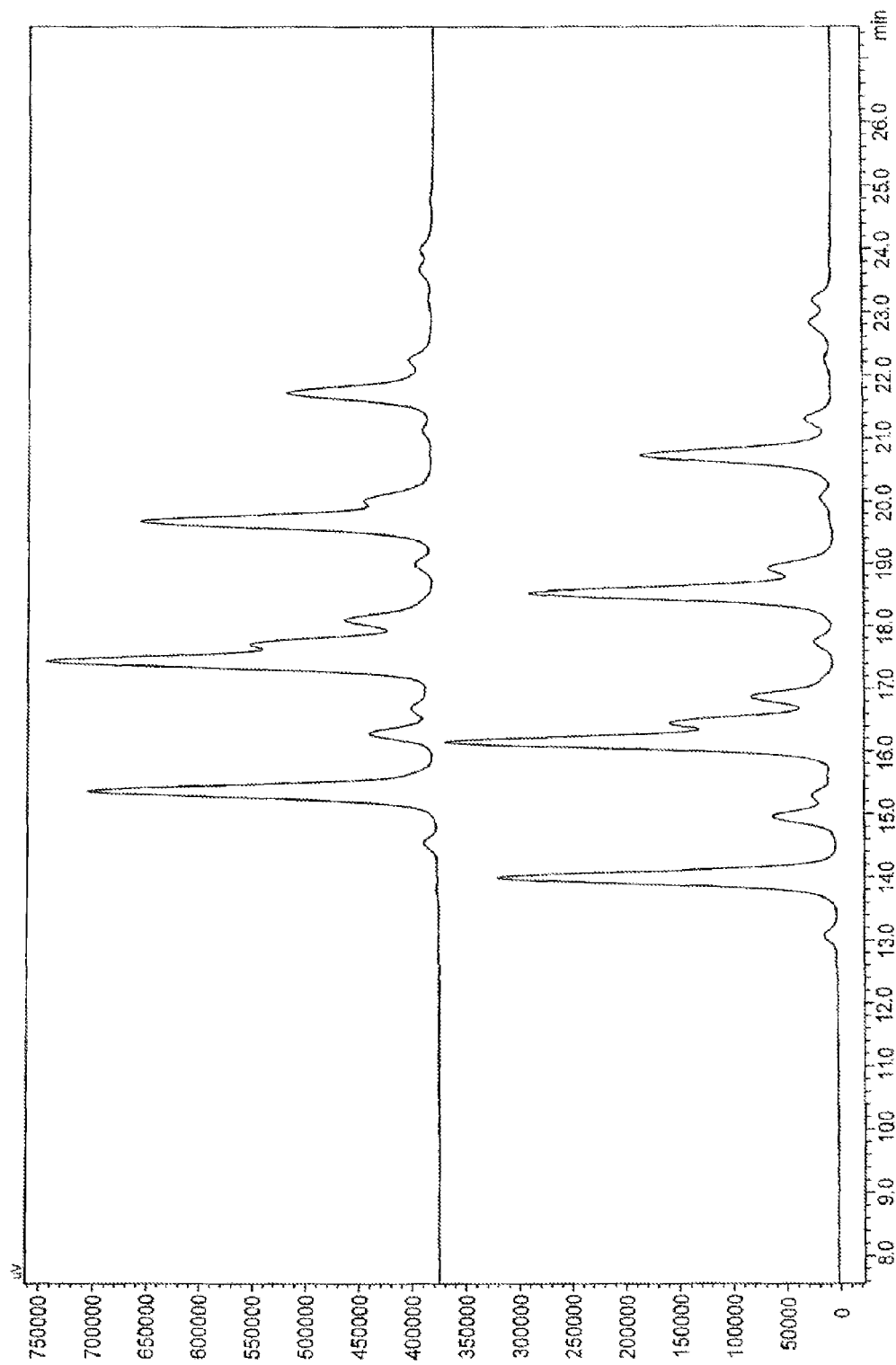
FIG. 8 shows a comparison of 4-AASC (upper) and 4-ABSC (lower) labeled N-glycans from human polyclonal IgG by HPLC hydrophilic interaction chromatography on Glycosep N-Plus HPLC column.

FIG. 8 shows a comparison of HPLC profiles of 4-AASC (upper) and 4-ABSC (lower) labeled N-glycans from human polyclonal IgG. N-glycans of human polyclonal IgG were enzymatically released using PNGase F and subjected to rapid fluorescent labeling with 4-ABSC or 4-AASC dye. After clean up of N-glycans from the excess of a dye, N-glycans were analyzed by HILIC HPLC with fluorescence detection (using excitation and emission wavelengths suitable for given dye).

Although the foregoing invention has been described in some detail by way of illustration and example for purposes of clarity of understanding, one with skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of rapid fluorescent labeling of N-glycans for analysis, said method comprising: contacting a compound of formula I:

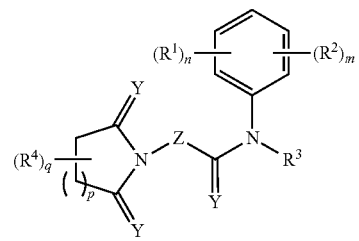

with N-glycans under conditions sufficient to form N-glycans labeled with a moiety:

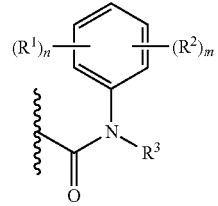

wherein:
the wavy line indicates the point of attachment to the rest of the molecule;
each Y is independently O= or S=;
Z is —O— or —S—;
either the subscript n=1-4 and each $R^1$ is independently selected from the group consisting of $C_{1-8}$alkyl, $C_{1-8}$heteroalkyl and aryl, and wherein adjacent $R^1$ groups together with the benzene ring to which they are attached form a fused carbocyclic aromatic ring system selected from the group consisting of naphthalene, phenanthrene, anthracene, triphenylene and pyrene, each of which having from 1-4 $R^5$ substituents selected from the group consisting of —COOH, —COO$^{31}$ M$^+$, sulfo, alkylsulfo, phosphono and alkylphosphono;
or n is zero;
each $R^2$ is independently selected from the group consisting of —$CO_2R^a$, —CN, —$NO_2$, —$N_3$, —N=C=O, —N=C=S, —NO, —N=C=NR$^a$, —S(O)R$^a$, —S(O)$_2$R$^a$, —S(O)$_2$NR$^a$R$^b$, —C(O)NR$^a$R$^b$, —C(O)R$^a$, —C(O)SR$^a$, —C(=S)R$^a$, —S—CN, sulfo, phosphono, alkylphosphono, and alkylsulfo, wherein $R^a$ and $R^b$ are each independently selected from the group consisting of —H, alkyl, aryl, arylalkyl, cycloalkyl, heteroalkyl and haloalkyl or optionally $R^a$ and $R^b$ when attached to the same nitrogen atom are combined to form a 5-or 6-membered ring having from 0-2 additional heteroatoms as ring members selected from O, N and S;

$R^3$ is —H or $C_{1-8}$alkyl;

each $R^4$ is independently $C_{1-8}$alkyl;

the subscript m is an integer from 1-5;

the subscript p is 1 or 2; and the subscript q is zero or an integer from 1-4.

2. The method of claim 1, wherein the N-glycans are generated in situ from the cleavage of glycoproteins by an enzyme.

3. The method of claim 1, wherein the N-glycans are present in an elution step.

4. The method of claim 2, wherein the enzyme is peptide-N4-(acetyl-β-glucosaminyl)-asparagine amidase.

5. The method of claim 2, wherein the N-glycans are β-glycosylamines.

6. The method of claim 1, wherein the contacting is in the presence of detergents and/or reductants.

7. The method of claim 1, wherein the contacting is at temperatures from about 5° C. to about 60° C.

8. The method of claim 1, wherein the contacting is in an aqueous environment.

9. The method of claim 1, wherein the contacting is for about 0.5 millisecond to about 10 minutes.

10. The method of claim 1, wherein the contacting is carried out at a pH greater than 7.

11. The method of claim 10, wherein the contacting is carried out at a pH from about 8 to about 12.

12. The method of claim 1, wherein the contacting is carried out at a pH less than 7.

13. The method of claim 1, wherein the contacting is carried out at a pH of 7.

14. A method of analyzing N-glycans, said method comprising:

i) contacting a compound of formula I:

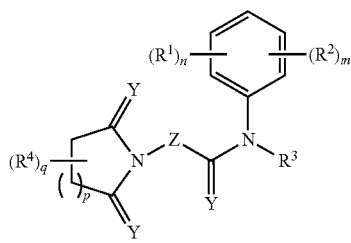

I with N-glycans under conditions sufficient to form labeled N-glycans, wherein
the N-glycans are labeled with a moiety:

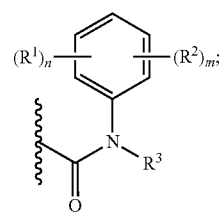

and (ii) providing the labeled N-glycans to an analytical means;

wherein:

the wavy line indicates the point of attachment to the rest of the molecule;

each Y is independently O= or S=;

Z is —O— or —S—;

either n=1-4; and each $R^1$ is independently selected from the group consisting of $C_{1-8}$alkyl, $C_{1-8}$heteroalkyl and aryl, and wherein adjacent $R^1$ groups together with the benzene ring to which they are attached form a fused carbocyclic aromatic ring system selected from the group consisting of naphthalene, phenanthrene, anthracene, triphenylene and pyrene, each of which having from 1-4$R^5$ substituents selected from the group consisting of —COOH, —COO$^{31}$ M$^+$, sulfo, alkylsulfo, phosphono and alkylphosphono;

or n is zero;

each $R^2$ is independently selected from the group consisting of —CO$_2$R$^a$, —CN, —NO$_2$, —N$_3$, —N=C=O, —N=C=S, —NO, —N=C=NR$^a$, —S(O)R$^a$, —S(O)$_2$R$^a$, —S(O)$_2$NR$^a$R$^b$, —C(O)NR$^a$R$^b$, —C(O)R$^a$, —C(O)SR$^a$, —C(=S)R$^a$, —S—CN, sulfo, phosphono, alkylphosphono, and alkylsulfo, wherein R$^a$ and R$^b$ are each independently selected from the group consisting of —H, alkyl, aryl, arylalkyl, cycloalkyl, heteroalkyl and haloalkyl or optionally R$^a$ and R$^b$ when attached to the same nitrogen atom are combined to form a 5-or 6-membered ring having from 0-2 additional heteroatoms as ring members selected from O, N and S;

$R^3$ is —H or $C_{1-8}$alkyl;

each $R^4$ is independently $C_{1-8}$alkyl;

the subscript m is an integer from 1-5;

the subscript p is 1 or 2; and the subscript q is zero or an integer from 1-4.

15. The method of claim 14, wherein said providing is injecting.

16. The method of claim 14, wherein said analyzing is selected from the group consisting of high-pressure liquid chromatography (HPLC), capillary electrophoresis gel, microfluidic separation and mass spectrometry.

17. The method of claim 16, wherein the HPLC is a reverse phase or a normal phase HPLC.

18. The method of claim 16, wherein the analyzing is by capillary electrophoresis.

19. The method of claim 1, wherein the compound has the formula Id:

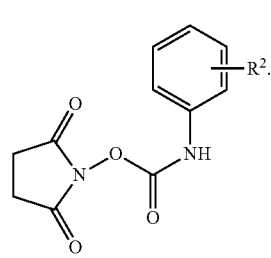

Id

20. The method of claim 14, wherein the compound has the formula Id:

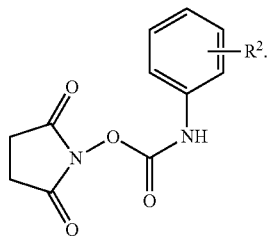

Id

21. The method of claim 19, wherein $R^2$ is —COOR$^a$.
22. The method of claim 21, wherein $R^2$ is —COOH or —CONH$_2$.
23. The method of claim 20, wherein $R^2$ is —COOR$^a$.
24. The method of claim 23, wherein $R^2$ is —COOH or —CONH$_2$.
25. The method of claim 1, wherein the compound is selected from the group consisting of:

Ig

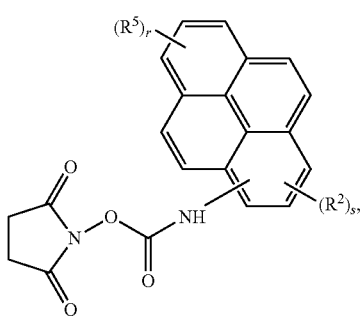

Ih

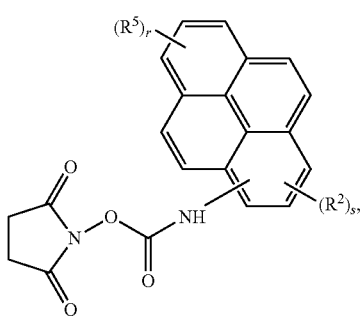

Ii

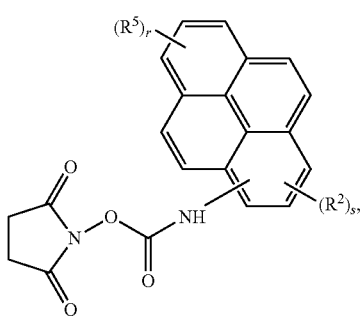

Ij

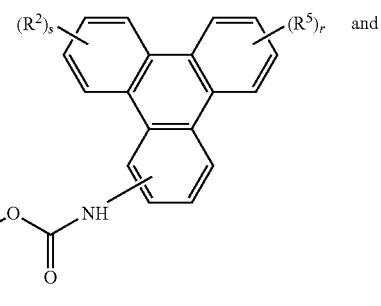

and

Ik

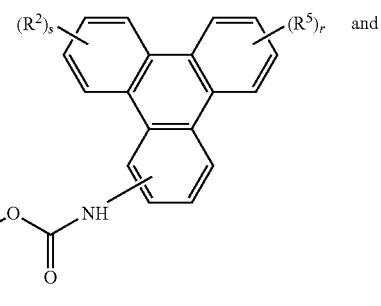

wherein each of $R^2$ and $R^5$ is independently selected from the group consisting of —COOH, sulfo, alkylsulfo, phosphono and alkylphosphono;

each r is independently an integer from 0-2; and each s is independently an integer from 0-3, with the proviso that r and s are not simultaneously 0; and the sum of r and s is between 1 and 4.

26. The method of claim 14, wherein the compound is selected from the group consisting of:

Ig

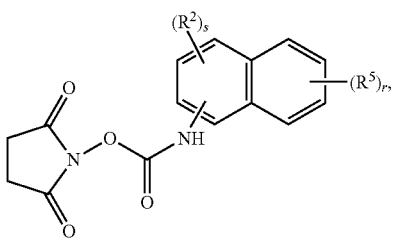

Ih

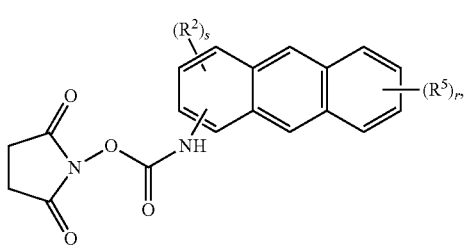

-continued

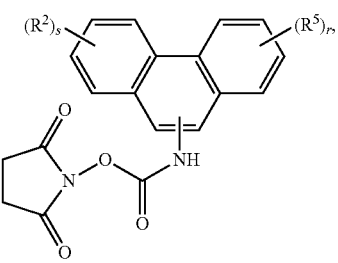

Ii

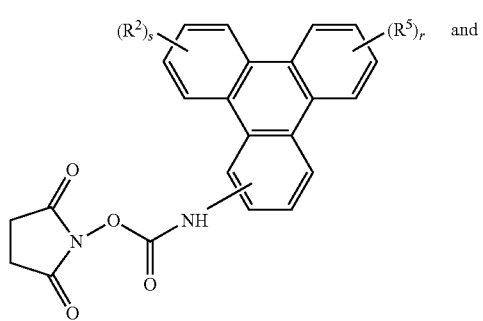
and

Ij

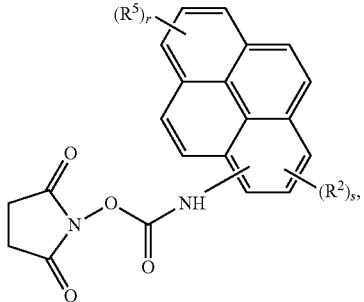

Ik wherein
each of $R^2$ and $R^5$ is independently selected from the group consisting of —COOH, sulfo, alkylsulfo, phosphono and alkylphosphono;
each r is independently an integer from 0-2; and
each s is independently an integer from 0-3, with the proviso that r and s are not simultaneously 0; and the sum of r and s is between 1 and 4.

27. The method of claim 14, further comprising detecting a fluorescent signal from the labeled N-glycans.
28. The method of claim 21, wherein $R^2$ is —CONH$_2$.
29. The method of claim 23, wherein $R^2$ is —CONH$_2$.
30. The method of claim 28, further comprising detecting a fluorescent signal from the labeled N-glycans.
31. The method of claim 29, further comprising detecting a fluorescent signal from the labeled N-glycans.

* * * * *

UNITED STATES PATENT AND TRADEMARK OFFICE
CERTIFICATE OF CORRECTION

PATENT NO. : 8,445,292 B2  
APPLICATION NO. : 13/244454  
DATED : May 21, 2013  
INVENTOR(S) : Tomasz Baginski Page 1 of 1

It is certified that error appears in the above-identified patent and that said Letters Patent is hereby corrected as shown below:

In the Claims:

Claim 1, col. 32, line 56 should read:
group consisting of -COOH, -COO⁻M⁺, sulfo, Claim 14, col. 34, line 16 should read:
-COOH, -COO⁻M⁺, sulfo, alkylsulfo, Signed and Sealed this
Ninth Day of July, 2013

Teresa Stanek Rea
*Acting Director of the United States Patent and Trademark Office*